(12) United States Patent
Woodward et al.

(10) Patent No.: US 9,002,151 B2
(45) Date of Patent: Apr. 7, 2015

(54) SYSTEM AND METHOD FOR NONLINEAR OPTICAL DEVICES

(71) Applicant: Telcordia Technologies, Inc., Piscataway, NJ (US)

(72) Inventors: Ted Woodward, Holmdel, NJ (US); Anjali Agarwal, Matawan, NJ (US); Nicholas Peters, Laurel, MD (US)

(73) Assignee: Telcordia Technologies, Inc., Piscataway, NJ (US)

( * ) Notice: Subject to any disclaimer, the term of this patent is extended or adjusted under 35 U.S.C. 154(b) by 259 days.

(21) Appl. No.: 13/646,450

(22) Filed: Oct. 5, 2012

(65) Prior Publication Data

US 2013/0089888 A1     Apr. 11, 2013

Related U.S. Application Data

(60) Provisional application No. 61/543,587, filed on Oct. 5, 2011.

(51) Int. Cl.

| | |
|---|---|
| *G02B 6/24* | (2006.01) |
| *G02F 1/365* | (2006.01) |
| *G01J 3/45* | (2006.01) |
| *G01N 21/17* | (2006.01) |
| *H01L 31/0232* | (2014.01) |
| *G01J 1/42* | (2006.01) |
| *G02B 6/293* | (2006.01) |
| *G01J 3/453* | (2006.01) |
| *G01J 1/04* | (2006.01) |

(Continued)

(52) U.S. Cl.
CPC ............ *G01N 21/17* (2013.01); *H01L 31/0232* (2013.01); *G01J 1/42* (2013.01); *G02B 6/29338* (2013.01); *G01J 3/4531* (2013.01); *G01J 1/0425* (2013.01); *G01N 21/41* (2013.01); *G01J 1/0459* (2013.01); *G01J 1/58* (2013.01); *G02F 1/3536* (2013.01); *G02F 2001/392* (2013.01); *G01S 17/10* (2013.01); *G01S 7/486* (2013.01); *G01S 7/487* (2013.01); *H04B 10/70* (2013.01)

(58) Field of Classification Search
CPC .......... G02F 1/3536; G02B 6/29338–6/29343; G01J 3/4531
See application file for complete search history.

(56) References Cited

U.S. PATENT DOCUMENTS

| | | |
|---|---|---|
| 4,912,526 A | 3/1990 | Iwaoka |
| 5,151,965 A | 9/1992 | Rikken |

(Continued)

FOREIGN PATENT DOCUMENTS

WO     2010/041042 A1     4/2010

*Primary Examiner* — Jerry Rahll

(57) ABSTRACT

Systems for enhancing the sensitivity of detecting an optical signal using nonlinear optics and method of performing the same. In one embodiment, a single-photon detection system includes an optical amplifier realized in a waveguide, and a photodetector coupled to an output of the optical amplifier. A light detection and ranging system includes the optical amplifier coupled to an optical source and one photodetector. In another embodiment, a photodetection system includes a plurality of optical frequency converters, coupled to an optical source, that sequentially convert a wavelength of photons of the optical source to a final wavelength, and a single-photon photodetector coupled to the optical frequency converters to detect single photons produced by the optical source. In another embodiment, an optical sensor includes an optical pump, and a transducer including an optical ring cavity coupled to the optical pump and configured to utilize optical four-wave mixing to detect an external stimulus.

20 Claims, 11 Drawing Sheets

(51) Int. Cl.
*G01N 21/41* (2006.01)
*G01J 1/58* (2006.01)
*G02F 1/35* (2006.01)
*G01S 17/10* (2006.01)
*G01S 7/486* (2006.01)
*G01S 7/487* (2006.01)
*H04B 10/70* (2013.01)
*G02F 1/39* (2006.01)

(56) References Cited

U.S. PATENT DOCUMENTS

| | | | |
|---|---|---|---|
| 5,742,633 A * | 4/1998 | Stone et al. ............ 372/92 | |
| 6,014,237 A | 1/2000 | Abeles | |
| 6,501,065 B1 | 12/2002 | Uppal | |
| 6,717,718 B1 | 4/2004 | Kelsoe | |
| 6,897,434 B1 | 5/2005 | Kumar | |
| 7,088,824 B1 | 8/2006 | Takeuchi | |
| 7,227,955 B2 | 6/2007 | Trifonov | |
| 8,059,966 B2 | 11/2011 | Igarashi | |
| 8,103,172 B2 | 1/2012 | Peters | |
| 8,351,783 B2 | 1/2013 | Hirano | |
| 2002/0080475 A1 | 6/2002 | Cornelius | |
| 2003/0219258 A1 | 11/2003 | Ellis | |
| 2004/0091000 A1 | 5/2004 | Kuksenkov | |
| 2008/0037595 A1 | 2/2008 | Gankkhanov | |
| 2010/0014073 A1 | 1/2010 | Hashiguchi | |
| 2010/0103505 A1 | 4/2010 | McKinstrie | |
| 2011/0211244 A1 | 9/2011 | Peters | |
| 2012/0195333 A1 | 8/2012 | Huang | |

* cited by examiner

US 9,002,151 B2

SYSTEM AND METHOD FOR NONLINEAR OPTICAL DEVICES

This application claims the benefit of U.S. Provisional Application No. 61/543,587, entitled "System and Method for Nonlinear Optical Devices," filed on Oct. 5, 2011, which is incorporated herein by reference.

TECHNICAL FIELD

The present invention is directed, in general, to nonlinear optics and, more specifically, to enhancing the sensitivity of detecting an optical signal using nonlinear optics and method of performing the same.

BACKGROUND

Photodetection is a fundamental process to many sensing and communication applications, and achieving high sensitivity in photon detection is desirable. A highly sensitive detection process employs number-resolving detection of individual photons. Such detection is now possible with various levels of performance for photons of different wavelengths. Photonic detection, however, is far from ideal. Photon-counting detectors suffer from many shortcomings, and at wavelengths beyond about 1.55 micrometers ("µm"), the detectors are not available at all. At telecommunication wavelengths, the detectors are much worse in performance than at wavelengths compatible with silicon-based detectors, which are, in turn, not as good as photomultiplier tubes.

At the relatively low counting rates encountered in single-photon systems, a primary degradation mechanism for 1.55 µm single-photon detectors ("SPDs") is so-called "dark-counts." Dark counts mean a spontaneous avalanche of a Geiger-mode biased avalanche photo diode ("APD") that is the preferred structure for 1.55 µm single-photon detection. Dark counts from these detectors depend on a bias voltage applied to the detector, as does detection efficiency. Typically, one must sacrifice detection efficiency by lowering the Geiger-mode bias avalanche photo diode voltage to obtain a dark count rate low enough for use in single-photon counting applications. A bias point exists that optimizes detection efficiency and dark count. Dark count rates in silicon detectors are generally much lower than in other solid-state Geiger-mode avalanche photo diodes ("GmAPDs"), but further improvements in signal detection capability would provide enhanced detection capability over longer distances.

In many quantum info nation processing applications, the source of quantum signals is operated so as to avoid multi-photon effects. These sources operate at very low mean photon numbers, much less than one. Such low mean photon number signals coupled with low detection efficiency single-photon detectors makes detection even more challenging, and these systems can benefit significantly from enhanced sensitivity detectors. Enhancing the sensitivity of optical detection would be a valuable step in overcoming performance limitations of single-photon detectors at wavelengths commonly used (e.g., 1.55 µm) in telecommunication systems and in other photonic systems such as light detection and ranging systems.

A further area that exhibits sensitivity limitations relates to the use of resonant nonlinear optical biosensors. A particular biosensing application is concerned with identifying an unknown chemical species in solution. A known method for accomplishing this task is to attach a selective molecular sensor to a transducer element that can be read out with an optical signal. High selectivity is obtained by the molecular sensor, to which only a specific species to be detected (the analyte) will bind.

Limitations of these optical signal and chemical detection approaches have now become hindrances for general high sensitivity light detection applications, and for detection of chemical species in low concentrations. Accordingly, what is needed in the art are new approaches that overcome the deficiencies in the current solutions.

SUMMARY OF THE INVENTION

These and other problems are generally solved or circumvented, and technical advantages are generally achieved, by advantageous embodiments of the present invention, including systems for enhancing the sensitivity of detecting an optical signal using nonlinear optics and methods of performing the same. In one embodiment, a single-photon detection system includes an optical amplifier realized in a waveguide, and a photodetector coupled to an output of the optical amplifier. A light detection and ranging system includes the optical amplifier coupled to an optical source and one photodetector. In another embodiment, a photodetection system includes a plurality of optical frequency converters, coupled to an optical source, that sequentially convert a wavelength of photons of the optical source to a final wavelength, and a single-photon photodetector coupled to the optical frequency converters to detect single photons produced by the optical source. In another embodiment, an optical sensor includes an optical pump, and a transducer including an optical ring cavity coupled to the optical pump and configured to utilize optical four-wave mixing to detect an external stimulus.

The foregoing has outlined rather broadly the features and technical advantages of the present invention in order that the detailed description of the invention that follows may be better understood. Additional features and advantages of the invention will be described hereinafter, which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, reference is now made to the following descriptions taken in conjunction with the accompanying drawings, in which.

Corresponding numerals and symbols in the different figures generally refer to corresponding parts unless otherwise indicated, and may not be redescribed in the interest of brevity after the first instance. The FIGUREs are drawn to illustrate the relevant aspects of exemplary embodiments.

DETAILED DESCRIPTION OF ILLUSTRATIVE EMBODIMENTS

Figure 1:
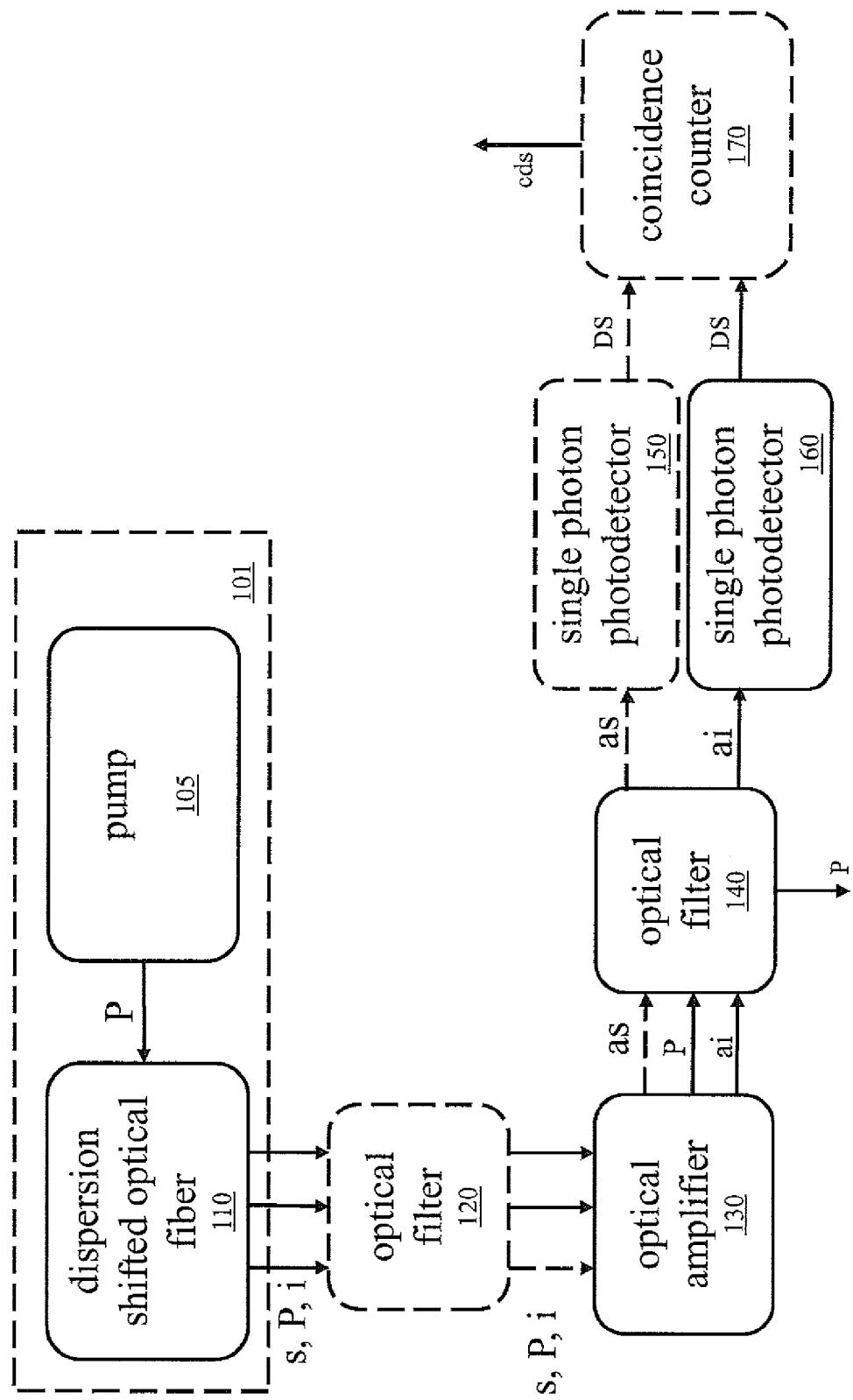
FIG. 1 illustrates a block diagram of an embodiment of a composite single-photon pair detector fanned with an optical amplifier followed by a photodetector.

The making and using of the present exemplary embodiments are discussed in detail below. It should be appreciated, however, that the embodiments provide many applicable inventive concepts that can be embodied in a wide variety of specific contexts. The specific embodiments discussed are merely illustrative of specific ways to make and use the systems, subsystems and modules associated with processes for detection of optical signals and chemical species.

Processes to allow detection of optical signals and chemical species employing nonlinear optical methods will be described. The processes will be described in specific contexts, namely techniques for photodetection including the use of photodetection techniques for detection of low levels of chemical species. While the principles will be described in an environment of photodetection of weak signals, any environment that may benefit from a process employing photodetection that enables detection of levels of photons in communication systems as well as the use of photonic techniques to detect low levels of chemical species is well within the broad scope of the present disclosure.

Optical parametric amplifiers ("OPAs") in fiber have been extensively studied in conventional practice with a focus on broadband wavelength conversion and similar applications. (See, "Wideband tuning of the gain spectra of one pump fiber optic parametric amplifier," by Marhic, et. al. J. Sel. Topics in Quantum Electronics, V. 10(5), pp. 1133-1141, 2004, which is incorporated herein by reference.) All of the systems have employed phase-insensitive configurations that, like erbium-doped fiber amplifiers ("EDFAs"), have a fundamental three decibel ("dB") noise-figure limit. A phase-insensitive amplifier inherently adds excess noise at an output thereof.

The optical phase-sensitive amplifier has a different working mechanism from that of a conventional optical parametric amplifier and exhibits an amplifier gain that depends on an optical phase relationship between input optical signals and a high power pump. This gives an optical parametric amplifier a unique potential for noiseless amplification (i.e., a zero decibel noise figure). (See, "Quantum Limits on Noise in Linear Amplifiers," by Caves, Phys. Rev. D., vol. 26, pp. 1817, 1982, and "Reduction of Quantum Fluctuation and Suppression of the Gordon-Haus Effect with Phase-sensitive Linear Amplifiers," by Yuen, Optics Lett., vol. 17, pp. 73-75, 1992, which are incorporated herein by reference.) It is preferable that an optical phase-sensitive amplifier adds no excess noise and hence is capable of providing improved noise performance. For a certain phase alignment relationship, the gain is maximized. Noise signals that do not possess phase alignment are amplified with a much smaller gain, which improves noise performance of the system. The phase relationship between the pump and the signal and the idler determines the optical gain, and it should be actively controlled. With an optical phase-sensitive amplifier, low photon count signals including single-photon pairs can be amplified without introducing excess noise.

Extensive work has been done with both phase-insensitive and phase-sensitive optical parametric amplifiers with classical input optical signals. Noiseless amplification has been demonstrated with classical signals in fiber optical phase-sensitive amplifier. (See, "Ultrasensitive Optical Links Enabled by Low-Noise Phase-sensitive Amplifiers," by Tong, et al., Nature Photon. 5, pp. 430-436, 2011, which is incorporated herein by reference.) Earlier work on fiber-based optical phase-sensitive amplifiers was centered on a frequency-degenerate signal and idler configuration and was implemented in an interferometer. (See, "Demonstration of Phase-regeneration of DPSK Signals Based on Phase-sensitive Amplification," by Croussore, et al., Opt. Express 13, pp. 3945-3950, 2005, and "Noise Figure of Phase-Sensitive Parametric Amplifier using a Mach-Zehnder Interferometer with Lossy Kerr Media and Noisy Pump," by Imajuku, et al., IEEE J. Quantum. Electron. 39, pp. 799-812, 2003, which are incorporated herein by reference.) More recently, frequency non-degenerate four-wave mixing-based fiber optical phase-sensitive amplifiers have been investigated for various applications in fiber communication systems such as in-line amplification and in regeneration of phase-encoded signals. (See, "Gain Characteristics of a Frequency Nondegenerate Phase-sensitive Fiber-optic Parametric Amplifier with Phase Self-stabilized. Input," by Tang, et al., Opt. Express 13(26), pp. 10483-10493, 2005, "Detailed Characterization of a Fiber-optic Parametric Amplifier in Phase-sensitive and Phase-insensitive Operation," by Kakanade, et al., Opt. Express 18, pp. 4130-4137, 2010, and "All-optical Phase and Amplitude Regenerator for Next-generation Telecommunications Systems," by Slavik, et al., Nature Photon. 4, pp. 690-695, 2010, which are incorporated herein by reference.) Conventional practice amplifies an unknown quantum state (also called cloning). (See, "Quantum Cloning with an Optical Fiber Amplifier," by Fasel, et al. Phys. Rev Lett. 89, p. 107901, 2002, and U.S. Patent Application Serial No. 2010/0177297, entitled "Systems and Methods for Quantum Receivers for Target Detection using a Quantum Optical Radar," to Guha, et al., published Jul. 15, 2010, which are incorporated herein by reference.) As introduced herein, photon pairs are amplified after their quantum state has been analyzed and accordingly the quantum state has been collapsed into a known state.

To operate an optical parametric amplifier in a phase-sensitive manner requires the presence of at least three waves at the input of the optical phase-sensitive amplifier, which can be achieved in two configurations. (See, "Phase-sensitive Amplification in a Fiber," by McKinstrie, et al., Opt. Express 12, pp. 4973-4979, 2004, which is incorporated herein by reference.) The first configuration requires a high power pump and a signal and idler with wavelengths symmetrically related to the central pump. The four-wave mixing process may be thought of as two pump photons destroyed to create one signal and one idler photon. The second configuration requires a signal and two pumps with wavelengths symmetrically related to the signal wavelength. In this case, the four-wave mixing process may be thought of as one photon from each of the two pumps being destroyed to create two signal photons.

The gain of an optical phase-sensitive amplifier can be obtained from parametric amplification equations. (See, "Nonlinear fiber optics," by Agrawal, Academic Press, San Diego, 1995, which is incorporated herein by reference.) It is assumed that the pump, signal and idler are co-polarized. Also, pump depletion and linear propagation losses are neglected and continuous wave ("CW") operation is assumed. Thus, the signal (As(z)) and idler (Ai(z)) output field operators after a distance z and the corresponding signal gain for the single pump and non-degenerate signal and idler configuration are:

$$A_s(z) = \mu A_s(0) + \nu A_i^+(0)$$

$$A_i(z) = \mu A_i(0) + \nu A_s^+(0),$$

$$G_{psa} = (|\mu|^2 + |\nu|^2) + 2|\mu\nu|\cos(\theta_\nu - \theta_\mu - \theta_s - \theta_i),$$

$$\mu = e^{\frac{i}{2}[\Delta\beta + 2\gamma P]z}\left\{\cosh(gz) - \frac{i}{2g}(\Delta\beta - 2\gamma P)\sinh(gz)\right\};$$

$$\nu = ie^{\frac{i}{2}[\Delta\beta + 2\gamma P]z}\frac{\gamma P}{g}e^{2i\theta_P}\sinh(gz).$$

As(0) and Ai(0) are the signal and idler fields at the input. Further, $$|\mu|^2 - |\nu|^2 = 1,$$

$\kappa = \Delta\beta + 2\gamma P_p$ is the phase mismatch, $\Delta\beta = \beta_s + \beta_i - 2\beta_p$ is the linear phase mismatch between signal, idler and pump ($\beta_s$, $\beta_i$, and $\beta_p$ are the respective propagation constants), $\gamma$ is the nonlinear coefficient, $g = [(\gamma P_p)^2 - (\kappa/2)^2]^{0.5}$, and $\theta = \phi_s + \phi_i - 2\phi_p$ is the relative phase difference between pump, signal and idler at the input of the phase-sensitive amplifier ("PSA").

For perfect phase-matching $\kappa = 0$ and the maximum gain is obtained for $\theta = \pi/2$ (in-phase gain) and $G_{max} = \exp(2\gamma P_p L)$. The maximum gain has an exponential dependence on pump power for perfect phase-matching. To obtain the condition $\kappa = 0$, it is required that:

$$2\gamma P_p = -\Delta\beta.$$

For perfect phase matching, the linear phase mismatch $\Delta\beta$ has to cancel the nonlinear phase shift due to self-phase modulation ("SPM") on the pump ($2\gamma P_p$). This condition implies that the pump is selected in the anomalous dispersion regime of the $\chi^{(3)}$ (also referred to as "Chi(3)") nonlinear material where a negative $\Delta\beta$ can cancel the positive nonlinear phase shift. Furthermore, in a Chi(3) material such as standard dispersion shifted fiber, to prevent signal walk-off, it is advantageous to operate close to the zero dispersion wavelength of the fiber. Phase matching depends strongly on the dispersion properties of the material and it might not always be possible to be perfectly phase-matched. Even under these conditions gain is possible. For $\kappa \neq 0$, such that $\kappa = 2\gamma P_p$ (i.e., $\Delta\beta = 0$) and $\theta = \pi/2$, the gain grows quadratically with $\gamma PL$ and is given by:

$$G^{\kappa \neq 0} = 1 + 2\gamma PL + 2(2\gamma PL)^2.$$

The maximum gain for a Chi(3) phase-insensitive parametric amplifier is lower than that of a phase-sensitive amplifier and can be approximated by:

$$G_{pia} = |\mu|^2 \approx G^{max}_{psa}/4.$$

Optical materials with $\chi^{(2)}$ (also referred to as "Chi(2)") nonlinearities are attractive because the materials generally have higher effective nonlinearity than materials with Chi(3) nonlinearities; however, the materials have drawbacks. Typically, Chi(2) materials include long periodically poled structures which should be precisely temperature tuned to maintain the phase matching conditions required for parametric amplification.

In addition, pump-signal frequency detuning in Chi(2) parametric processes is typically very large, thus placing strict requirements on system parameters. In contrast, such restrictions are not necessary when employing Chi(3) materials. Further, the output of the parametric amplifier should often be coupled into a single mode optical fiber. Employing Chi(2) nonlinearity is further disadvantageous as it is difficult to achieve high coupling efficiency, which results in a significant reduction of net amplifier gain, thus degrading system performance.

In a Chi(3) waveguide such as dispersion shifted fiber, photons are naturally generated in a single spatial mode of the fiber, which results in increased stability, lower loss and ease of phase-matching. The lower effective nonlinearity of Chi(3) materials (such as dispersion shifted fiber ("DSF")) employs the use of long (hundreds of meters of) lengths to obtain sufficiently high gain. However, newer Chi(3) materials with higher nonlinearity have been developed that include highly nonlinear fiber, photonic crystal fiber, bismuth oxide doped nonlinear fiber, chalcogenide glass, etc., in which optical parametric amplifiers (again, mostly for wavelength conversion) have been demonstrated. (See, Continuous Wave Wavelength in a Photonic Crystal Fiber with Two Zero Dispersion Wavelengths," by Andersen, et al., Optics Express, v.12(17), pp. 4113-4122, 2004, "Chalcogenide Glass Advanced for All-Optical Processing", by Eggleton, et al., Photonics Spectra, September 2007, and "Bismuth Oxide Based Nonlinear Fiber with a High SBS Threshold and its Application to Four Wave Mixing Wavelength Conversion using a Pure Continuous Wave Pump," by Lee, et al., J. Lightwave Tech., v. 24(1), pp. 22-28, 2006, which are incorporated herein by reference.) In recent years optical parametric amplifiers have also been demonstrated in integrated resonant silicon structures making them compact and significantly improving peak pump power requirements. (See, "Ultra-low Power Parametric Frequency Conversion in a Silicon Microring Resonator," by Turner, et al., Optics Express, vol. 16, pp. 4881-4887, 2008, which is incorporated herein by reference.) In addition, these materials can be engineered so that the dispersion is enhanced for improved phase-matching in the parametric amplifier. The use of Chi(3) nonlinear waveguides is thus particularly advantageous over an optical material with Chi(2) nonlinearity.

A process is introduced for single-photon/single-photon pair photodetector performance enhancement through the use of an ultra-low noise optical phase-sensitive amplifier as a preamplifier. A phase-insensitive parametric optical amplifier can also be employed. The process can be employed in, for example, a light detection and ranging system. The use of nonlinear optics enhances detection sensitivity, suppresses noise, and improves performance of photon detection systems such as light detection and ranging systems as well as single-photon detection arrangements in the mid-infrared ("mid-IR") wavelength range.

As introduced herein, a light detection and ranging system is formed with an optical amplifier. An optical parametric amplifier can also be employed for amplification. Key differences from conventional practice include the use of a Chi(2) optical parametric amplifier for amplification in the prior art before a photodetector. The use of a Chi(3) optical phase-sensitive amplifier as introduced herein provides an advantage in performance over a Chi(2) optical parametric amplifier.

The conventional systems use Chi(2) material to construct an optical parametric amplifier. As indicated above, the process in a Chi(3) material utilizes four-wave mixing, and there are significant advantages of Chi(3) nonlinearity over a Chi(2) nonlinearity. Summarizing, key advantages of Chi(3) nonlinearity over Chi(2) nonlinearity include ability to have dispersion engineered fiber optic materials, which is important for phase-matching, ease of phase-matching in a waveguide, low loss, highly robust and stable, and ability to have small detuning between pump and signal frequencies.

As introduced herein, an optical amplifier is implemented in a waveguide with Chi(3) nonlinearity and single-photon pairs are detected. An idler may be retained, but not required according to conventional practices. In an embodiment, signal and idler are both transmitted, which avoids the need to delay the idler as performed in conventional practice. An embodiment of an optical phase-sensitive amplifier is implemented with 400 meters ("m") of dispersion shifted fiber ("DSF"). The dispersion shifted fiber is fiber whose zero-dispersion wavelength has been engineered to be, for instance, in the 1.55 µm region. The input optical signal to the optical phase-sensitive amplifier is a quantum signal that can be a sequence of single-photon pairs generated from a single-photon source. Using a pulsed pump centered at a wavelength close to the zero dispersion wavelength of the fiber, an experimental gain of 4.6 decibels was measured classically by using an optical spectrum analyzer ("OSA"). This gain is consistent with a gain measured through "singles" and "coincidence" counts of a signal and idler photon pair on individual single-photon detectors. Here, "singles" means a measurement of single events arising on each single-photon detector from signal and idler photons. "Coincidence" counts means that substantially simultaneous counts are obtained from a signal (designated "s") and idler (designated "i") photon pair during a gate interval on the two single-photon detectors.

The results of optical spectrum analyzer measurements for both phase-sensitive and phase-insensitive amplifier configurations were experimentally compared. The gain for the phase-sensitive amplifier configuration is higher than a phase-insensitive amplifier configuration. The optical phase-sensitive amplifier gain of 4.6 decibels had a standard deviation of 0.3 decibels and a gain of 2.9 decibels for a phase-insensitive parametric amplifier with a standard deviation of 0.35 decibels was measured. Thus, the gain of an optical phase-sensitive amplifier may be employed to enhance single-photon detection performance when operated as a preamplifier. Changing to a phase-insensitive configuration results in a lower measured singles gain of about 3 decibels, confirming that a gain advantage can be achieved with an optical phase-sensitive amplifier over a phase-insensitive parametric amplifier.

Turning now to FIG. 1, illustrated is a block diagram of an embodiment of a composite single-photon pair detector formed with an optical amplifier (e.g., an optical preamplifier) followed by a photodetector. The optical amplifier can be an optical phase-sensitive amplifier or a parametric amplifier, and the photodetector can be a Geiger-mode avalanche photo diode that has a noise characteristic with noise amplitude inversely related to a probability of photon detection. In an embodiment, the photodetector can be a p-doped, intrinsic n-doped ("PIN") photodetector or a superconducting single-photon photodetector. These arrangements are highly beneficial for high-sensitivity detection systems such as in light detection and ranging applications and in quantum information processing applications where signals of interest are highly attenuated, usually by a path length. Each photodetector detects a single photon, but the system can react to a plurality of photons. A photodetector can respond to a sequence of photons produced by the optical amplifier. It is recognized that a photodetector does not detect every photon with unity probability. Thus, there is a need for amplification to improve detection probability and performance.

A single-photon pair source 101 is coupled to an optical amplifier 130 through an optional optical filter 120. The single-photon pair source 101 can be formed with a pump 105 that produces a pump signal P that is coupled to a dispersion shifted optical fiber 110. Signal "s", idler "i", and pump P signals are coupled to a dispersion shifted optical fiber 110, which exhibits total reflection of the optical signals at its circumferential surface and, accordingly, is a waveguide. The output of the dispersion shifted optical fiber 110 is coupled to the optical filter 120. The optical filter 120 is an optional element that may be omitted when the pre-amplifier is a parametric optical amplifier that is generally phase sensitive. The optical filter 120 strips the signal wavelength and passes pump and idler wavelengths. The output of the dispersion shifted optical fiber 110, or optionally the output of the optical filter 120, is coupled to the optical amplifier 130, which can be a parametric amplifier when only pump and idler signals are present, or a phase-sensitive optical amplifier when pump, signal, and idler are present and synchronized because they are all commonly conducted through a relatively short low-dispersion optical fiber.

The optical amplifier 130 can be formed with, for instance, 400 meters of dispersion shifted fiber, the length of which can be traded off with pump power. The amplification relies on nonlinearity of the dispersion shifted fiber (e.g., a refractive index/optical susceptibility that is wavelength dependent). The optical amplifier 130 is formed with a highly nonlinear fiber ("HNLF") such as a Chi(3) nonlinear optical material and can produce an output signal wavelength in response to two pump wavelengths distributed symmetrically on either side of a wavelength of the input optical signal coupled to the optical amplifier. The optical amplifier 130 can operate on a signal "s" with a signal wavelength and an idler "i" with an idler wavelength distributed symmetrically on either side of the central pump wavelength that is coupled to the optical amplifier. The optical amplifier 130 produces an amplified signal "as" and an amplified idler "ai" at an output thereof. The presence of a phase-synchronized signal "s" with an idler "i" improves the amplification capability of an optical phase-sensitive amplifier over that of a phase-insensitive optical parametric amplifier.

The output of optical amplifier 130 is coupled to optical filter 140 that strips away pump wavelengths from a pump P signal and provides separate outputs for signal and idler wavelengths. The separated amplified signal "as" when it is present is coupled to a first single-photon detector 150, and the separated amplified idler "ai" is coupled to a second single-photon detector 160. The first and second single-photon detectors 150, 160 count photons over a period of time and can be formed from single photon detectors such as Geiger mode avalanche photodiodes superconducting transition edge photodetectors, or nanowire photodetectors. The first and second single-photon detectors 150, 160 can detect a single photon, but the system reacts to a plurality of photons, and each of the first and second single-photon detectors 150, 160 can respond to many photons produced by the optical amplifier 130. It is recognized that the first and second single-photon detectors 150, 160 do not detect every photon with unity probability. Thus, there is generally a need for amplification to improve detection probability.

The outputs (detected signals DS) of the first and second single-photon detectors 150, 160 when both the amplified signal "as" and the amplified idler "ai" are present are coupled to coincidence detector 170 that time-correlates the amplified signal "as" and idler "ai" photon detections (detected signals DS) to produce a coincidence-detected signal cds. Thus, the arrangement of the first and second single-photon detectors 150, 160 is configured to measure a time-correlated coincidence between the amplified signal "as" and the amplified idler "ai".

An embodiment of an optical phase-sensitive amplifier was constructed for demonstration of enhancement of single-photon detector sensitivity at 1.55 µm and for quantum signals. A wavelength of 1.55 µm is a frequently used wavelength for telecommunications fiber-optic systems as well as for detection of quantum photonic signals. The optical phase-sensitive amplifier was constructed with optical fiber using glass materials with a Chi(3) nonlinear optical response and employing degenerate or non-degenerate signal and idler frequencies, referring to a third-order nonlinear polarization coefficient/optical susceptibility of the optical fiber. In an embodiment, the Chi(2) nonlinear material, referring to a second-order nonlinear polarization coefficient/optical susceptibility of the optical fiber, can be employed. A frequency non-degenerate configuration in Chi(3) material generally requires both signal "s" and idler "i" to be present at the input of the optical phase-sensitive amplifier to obtain advantages of phase-sensitive signal detection.

FIG. 1 demonstrates an embodiment of an amplification configuration that can be used for enhancement of single-photon detector sensitivity. An unseeded optical parametric amplifier can be used to generate a single-photon pair at signal and idler frequencies. An embodiment of an optical parametric amplifier can be formed with 300 meters of dispersion shifted fiber and can be pumped with a mode-locked laser ("MLL") at a center frequency of 1554.1 nanometers ("nm") and with a pulse width of about five picoseconds ("ps") to generate the signal "s" and idler "i" at 1550.1 nm and 1558.1 nm, respectively, through a four-wave mixing ("FWM") process. The dispersion shifted fiber used has a zero-dispersion wavelength engineered to be in the 1.55 µm region, and dispersion zero wavelength close to the pump wavelength.

An embodiment of an optical phase-sensitive amplifier was implemented with a 400 meters long dispersion shifted fiber with a zero dispersion wavelength close to the pump wavelength, as described previously hereinabove. The three signals, the pump P, signal "s", and idler "i" signals, were input to an optical phase-sensitive amplifier for amplification of a signal and idler photon pair. As described previously hereinabove, the pump wavelength was filtered out by an optical filter 140, and the signal and idler wavelengths were separated by this filter using high-isolation technology. The first and second single-photon detectors 150, 160 based on thresholding were used to detect the amplified signal and idler photons.

The use of electronics allows measuring single-photon photon counts and also coincidence counts. Here, single-photon counts means a measurement of single-photonic events arising at the first and second single-photon detector 150, 160. Coincidence counts means that simultaneous counts from the signal "s" and idler "i" were obtained during a gating interval on the first and second single-photon detectors 150, 160. Accidental subtracted coincidences are estimated, which subtracts observed coincidences due to a desired signal "s" photon and an undesired noise photon from the total coincidences measured.

The detection efficiency of single-photon detectors was calibrated in an experimental set up and was 13 percent and 18 percent, respectively. An optical filter was inserted before the optical phase-sensitive amplifier to filter out the signal photon to enable comparison of gain performance of the optical phase-sensitive amplifier with that of a phase-insensitive parametric amplifier.

The mean photon number of the single-photon source can be estimated by calculating the probability of observing one photon and two photons for each of the signal and idler photons. For this the output signal (or the idler) is connected to a 50/50 optical splitter, the two outputs of which are connected to the single-photon detectors. The singles count is measured on each detector and the coincidence counts between simultaneous detection of signal-signal (or idler-idler) on the two detectors is also measured. Assuming a Poisson distribution for the arrival of photons, the probability of observing n photons with a mean photon number ρ is given by:

$$P[n, \rho] = \frac{\rho^n \cdot e^{-\rho}}{n!}.$$

Taking the ratio of the probability of observing two photons to that of observing one photon, normalized by detector efficiencies ($\eta 1, \eta 2$), $$\frac{P[2, \rho]}{P[1, \rho]} = \rho \left( \frac{\eta_1 \eta_2}{\eta_1 + \eta_2} \right)$$

is obtained.

From this relation the mean photon number ρ of the source is calculated based on the measurements. From the mean photon number ρ before and after the optical phase-sensitive amplifier, the gain can be estimated. The mean photon number ρ before the optical phase-sensitive amplifier was experimentally determined to be 0.06, confirming using single photons. After the optical phase-sensitive amplifier, the mean photon number was about 0.17, leading to an optical phase-sensitive amplifier gain of 4.6 decibels, which is consistent with the classical measurements. This higher mean photon number can be employed to compensate for the low detection efficiency of the single-photon detectors. For the phase-insensitive configuration, the gain was lower, 3.3 decibels.

Next, coincidence counts between the signal and the idler were measured in a composite detector formed with an optical phase-sensitive amplifier before single-photon detection at 1.55 µm. The gain seen by accidental subtracted signal-idler coincidence counts is higher than the singles gain. The benefit of coincidence measurement is about 1.2 decibels over the singles gain. The measured gain in the coincidence counts is smaller than expected mainly due to higher singles count from Raman noise and due to undercounting of the coincidence counts due to detector saturation. This occurs because the single-photon detectors are threshold detectors and not number-resolving detectors. A signal-idler coincidence gain of 5.8 decibels was experimentally measured. Undercounting of signal-idler coincidences is the main cause for the observation of a reduced gain in signal-idler coincidences.

Besides quantum communications, remote sensing employing photonics is another application where single-photon detectors can be employed because the received signals are highly attenuated and may be on the order of a few photons or even single photons. An optical parametric amplifier can be employed to enhance the detection performance in remote-sensing light detection and ranging systems. Either phase-sensitive or phase-insensitive parametric amplifiers can provide gain and hence increase a mean photon number at the detector. An advantage of phase-sensitive parametric amplifier is that the gain is higher and the noise performance is better. The gain in the accidental subtracted coincidences is higher than that of the singles count, which can be used to advantage in a light detection and ranging system by detecting signal and idler coincidences after the pre-amplifier.

Conventional light detection and ranging systems based on single-photon detectors do not employ optical pre-amplification at the receiver. Conventional light detection and ranging systems also do not employ a parametric source that generates a signal and idler through a process of four-wave mixing in a Chi(3) optical medium. Classical communication systems have successfully employed phase-insensitive amplifiers such as erbium-doped fiber amplifiers ("EDFAs") for pre-amplification. Using phase-sensitive amplifiers runs counter to conventional practices. Light detection and ranging systems based on single-photon detectors traditionally do not employ any optical pre-amplification at the receiver.

In an example, four-wave mixing is performed in a Chi(3) nonlinear photonic material. The use of Chi(3) over Chi(2) photonic materials is significantly advantageous. Conventional light detection and ranging systems do not employ a parametric source that generates signal and idler through the process of four-wave mixing in a Chi(3) optical material. In light detection and ranging systems, single-photon detectors offer sensitivity to measure a highly attenuated signal, but have poor detection efficiency at 1.55 μm. As introduced herein, an optical phase-sensitive amplifier gives the advantage of not only enhancing the detection efficiency through noiseless amplification of a return signal, but an even higher gain (and hence further enhanced efficiency) with signal-idler "coincidence" measurements.

Thus, a single-photon detection system and method of operating the same have been introduced herein. In one embodiment, the single-photon detection system includes an optical amplifier realized in a waveguide, and at least one photodetector coupled to an output of the optical amplifier. The photodetector may be a Geiger-mode avalanche photodiode having a noise characteristic with a noise amplitude inversely related to a probability of photon detection. The photodetector may be a p-doped, intrinsic n-doped ("PIN") photodetector or a superconducting single-photon detector. The optical amplifier may be an optical parametric amplifier or a phase-sensitive optical parametric amplifier.

The optical amplifier is configured to produce an amplified signal with a signal wavelength in response to two amplified pump signals with respective pump wavelengths distributed symmetrically on either side of the signal wavelength. The optical amplifier is configured to operate on a signal with a signal wavelength and an idler with an idler wavelength. The signal wavelength and the idler wavelength are distributed symmetrically on either side of a central pump wavelength coupled to the optical amplifier to produce an amplified signal and an amplified idler at an output thereof. The single-photon detection system may include two photodetectors configured to measure a time-correlated coincidence between the amplified signal and the amplified idler. The optical amplifier may include a Chi(3) nonlinear optical material.

Figure 2:
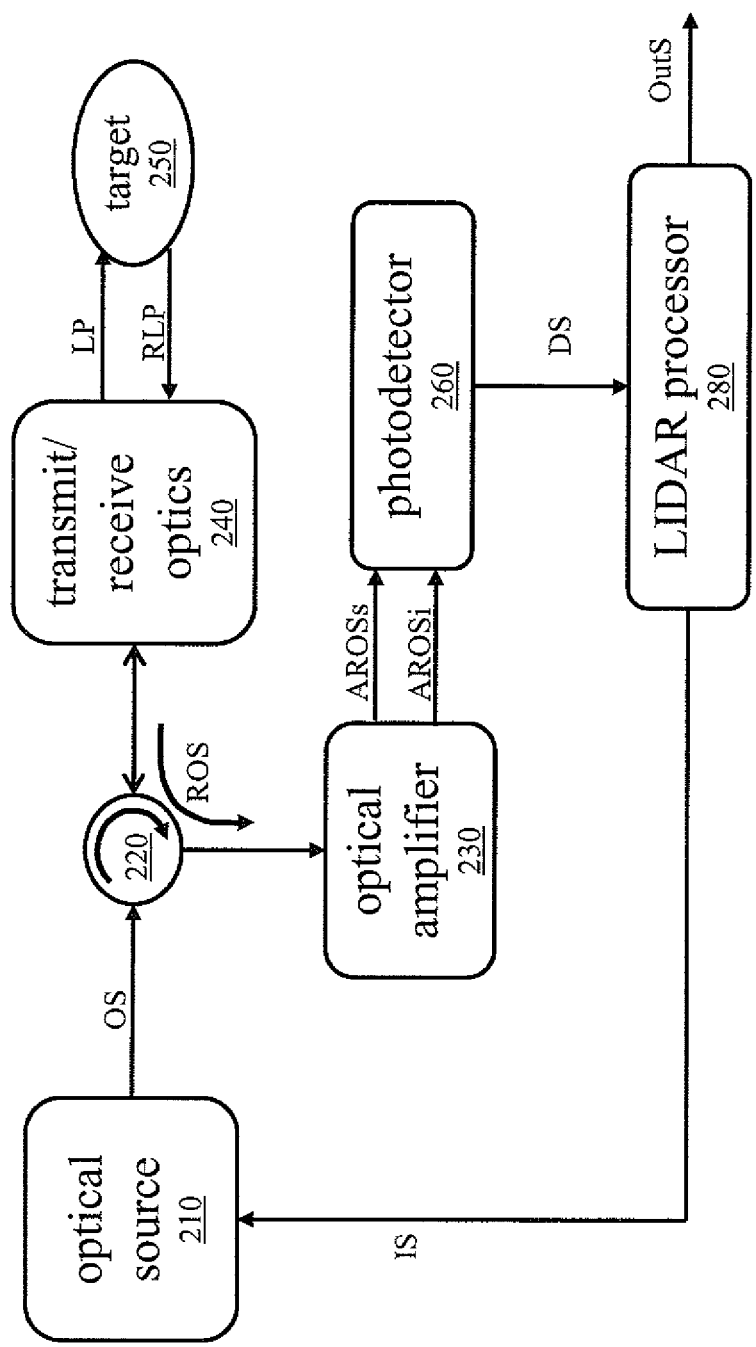
FIGS. 2 to 4 illustrate block diagrams of embodiments of light detection and ranging systems.

Turning now to FIG. 2, illustrated is a block diagram of an embodiment of a light detection and ranging ("LIDAR") system. The light detection and ranging system includes an optical amplifier 230 coupled to an optical source 210 through an optical circulator 220, and a photodetector 260 coupled to the optical amplifier 230. A photodetector 260 can be employed in light detection and ranging applications, and also in quantum communication applications, particularly in applications wherein a small signal is received. The optical amplifier 230 is realized in a waveguide. For example, the optical amplifier 230 can be constructed with an optical fiber operable as a waveguide wherein light is substantially internally totally reflected at a circumferential surface to enable the light to propagate nearly losslessly along a longitudinal fiber axis. The optical amplifier 230 can be constructed as a phase-sensitive amplifier or as an optical parametric amplifier.

The optical source 210 (e.g., a distributed feedback laser or a semiconductor laser) produces an input optical signal OS in response to an initiation signal IS produced by a light detection and ranging processor 280. The input optical signal OS includes an optical signal "s" and/or an optical signal "s" and an associated idler "i". The input optical signal OS is coupled to an optical circulator 220 (also referred to as a directional coupler), an output tap of which is coupled to transmit/receive optics 240. An outgoing light pulse LP produced by the transmit/receive optics 240 propagates in free space and bounces off a target 250, a distance to which is desired to be measured. A reflected light pulse RLP that bounced off the target 250 is captured by the transmit/receive optics 240 and is provided as a return optical signal ROS to optical circulator 220.

The optical circulator 220 couples the return optical signal ROS to the optical amplifier 230, which produces amplified return optical signals AROSs, AROSi for the photodetector 260. The photodetector 260 produces a detected signal DS in response to the amplified return optical signal(s) AROSs, AROSi. The detected signal DS is coupled to the light detection and ranging processor 280 that measures and provides an output signal OutS representing a round-trip time of the outgoing light pulse LP and the reflected light pulse RLP to estimate a distance of the target 250 from the transmit/receive optics 240.

Figure 3:
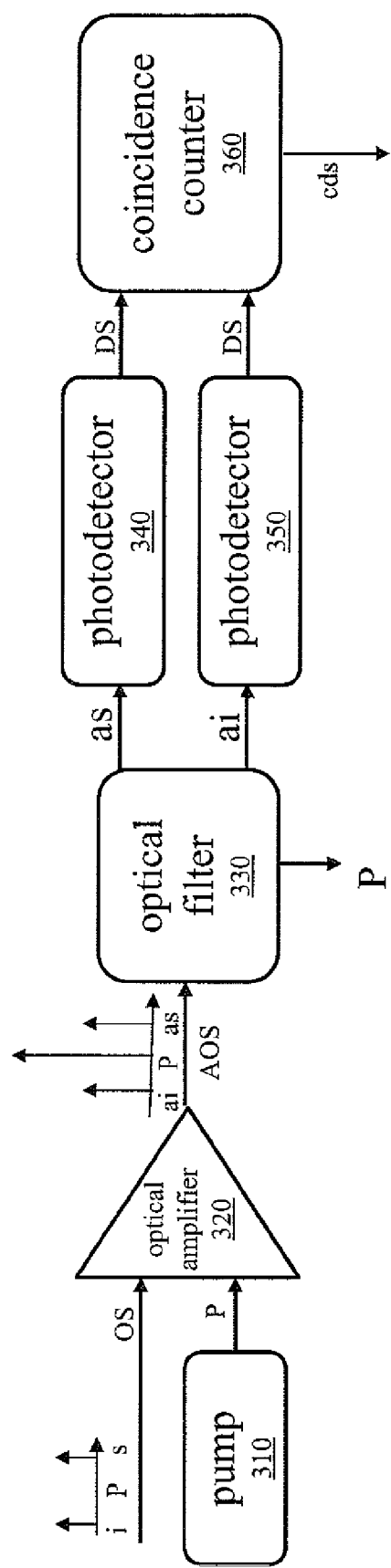

Turning now to FIG. 3, illustrated is a block diagram of another embodiment of a light detection and ranging ("LIDAR") system. The light detection and ranging system includes an optical amplifier 320 (e.g., an optical phase-sensitive amplifier) coupled through an optical filter 330 to first and second photodetectors 340, 350, that in turn are coupled to coincidence counter 360. The optical amplifier 320 may be constructed as an optical parametric amplifier, and can be constructed with nonlinear optical Chi(3) material. One input of the optical phase-sensitive amplifier 320 is coupled to an input optical signal OS that includes a signal "s" and an associated idler "i", with their respective wavelengths, that can be generated through an optical parametric process. A minimum input is a single signal "s" photon and a single associated idler "i" photon (i.e., a single signal-idler photon pair). Obviously, the process is operable with a plurality of signals "s" and associated idler "i" photons.

A central pump 310 (e.g., a distributed feedback laser or a semiconductor laser) produces a pump signal P that is coupled to another input of the optical amplifier 320. The wavelength of the pump signal P is centrally positioned between the signal "s" and the associated idler "i" (i.e., the wavelengths of the signal "s" and the associated idler "i" are symmetrically positioned about the wavelength of the pump signal P).

In response to the input optical signal OS and pump signal(s) P, the optical phase-sensitive amplifier 320 produces an amplified optical signal AOS including an amplified signal "as" and an amplified idler "ai" at an output thereof. The amplified optical signal AOS of the optical amplifier 320 is coupled to the optical filter 330 that separates the amplified signal "as" and the amplified associated idler "ai" and removes the pump signal P. The optical amplifier 320 operates with a four-wave mixing process, and can produce a plurality of output photons from an input of a single signal "s" photon and a single associated idler "i" photon, which have a phase relationship between them. The optical filter 330 can be constructed with wavelength division multiplexing ("WDM") technology.

The amplified signal "as" is coupled to an input of the first photodetector 340, an output of which is coupled to an input of coincidence counter 360. The amplified idler "ai" is coupled to an input of the second photodetector 350, an output of which is coupled to another input of coincidence counter 360. The first and second photodetectors 340, 350 can be constructed, without limitation, with Geiger-mode avalanche photodiodes, PIN photo diodes, or superconducting single-photon detectors. The Geiger-mode avalanche photodiode can have a noise mechanism dependent on a photodetector dark count. The coincidence counter 360 produces a coincidence detection signal cds upon detection of a time-correlated coincidence between detected signals DS for the amplified signal "as" and the amplified associated idler "ai".

Figure 4:
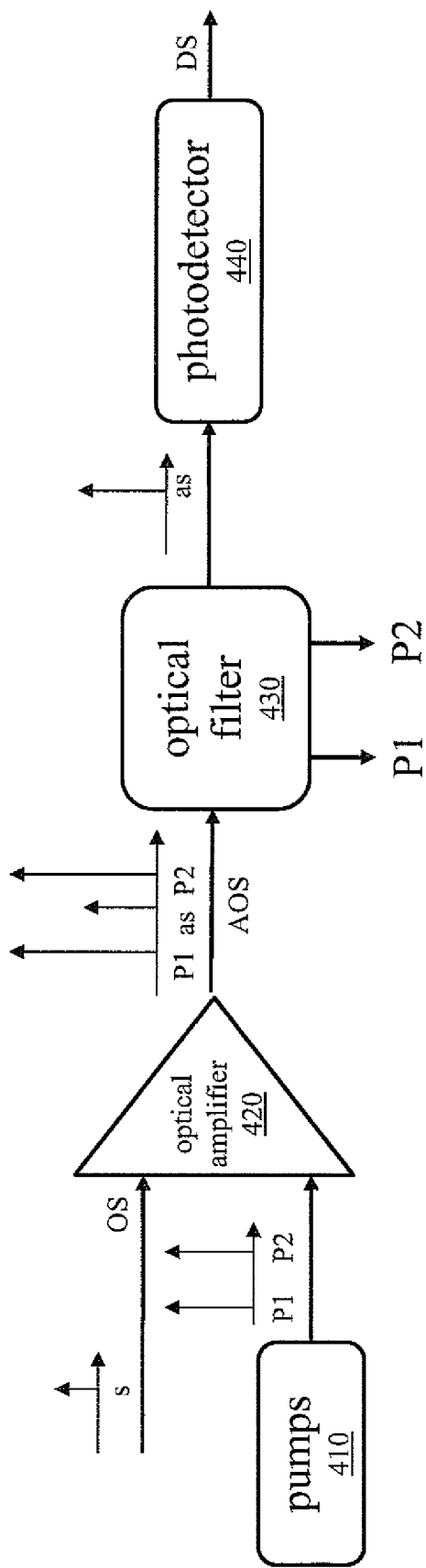

Turning now to FIG. 4, illustrated is a block diagram of another embodiment of a light detection and ranging ("LIDAR") system. The light detection and ranging system includes an optical amplifier 420 (e.g., an optical phase-sensitive amplifier) coupled through an optical filter 430 to a photodetector 440. The optical amplifier 420 may be constructed as an optical parametric amplifier, and can be constructed with nonlinear optical Chi(3) material. An input optical signal OS including a signal "s" is coupled to one input of the optical amplifier 420, and two pump signals P1, P2 produced by pumps 410 (e.g., distributed feedback lasers or semiconductor lasers) are coupled to another input of optical amplifier 420.

The optical amplifier 420 produces an amplified optical signal AOS including an amplified signal "as" and the two pump signals P1, P2 at an output thereof. The optical filter 430 separates the amplified signal "as" from the two pump signals P1, P2 to produce an amplified and separated signal "as". The amplified and separated signal "as" is coupled to an input of the photodetector 440, which produces a detected signal DS in response to the amplified and separated signal "as". The photodetector 440 can be constructed, without limitation, with Geiger-mode avalanche photodiodes, PIN photodiodes, or superconducting single-photon detectors. This embodiment provides the advantage of enhancing the detection efficiency through noiseless amplification of the return signal, but does not include the signal-idler "coincidence" measurements as obtained from the embodiment illustrated in FIG. 3.

Thus, a light detection and ranging system and method of operating the same have been introduced herein. In one embodiment, the light detection and ranging system includes an optical amplifier coupled to an optical source and realized in a waveguide, and at least one photodetector coupled to the optical amplifier. The light detection and ranging system may also include a central pump coupled to an input of the optical amplifier. The optical source is configured to generate an input signal with a signal wavelength and an input idler with an idler wavelength, wherein the signal wavelength and the idler wavelength are symmetrically related to a wavelength of the central pump. The signal wavelength and the idler wavelength may be generated through an optical parametric process. The optical amplifier is also configured to produce an amplified signal and an amplified idler at an output thereof from the input signal and the input idler. The light detection and ranging system may also includes two photodetectors configured to detect a time-correlated coincidence between the amplified signal and the amplified idler.

The light detection and ranging system may also include two pumps with respective pump wavelengths coupled to an input of the optical amplifier. The optical source is configured to generate an input signal with an input signal wavelength and the pump wavelengths are positioned symmetrically on either side of the input signal wavelength. The optical amplifier is configured to produce an amplified signal in response to the input signal.

The photodetector may be a Geiger-mode avalanche photodiode including a noise mechanism dependent on a dark count of the photodetector. The photodetector may be a p-doped, intrinsic n-doped photodetector or a superconducting single-photon detector. The optical amplifier may be an optical parametric amplifier or a phase-sensitive optical parametric amplifier. The optical amplifier may include a nonlinear optical Chi(3) material.

A process is now introduced by which low-photon count signals at mid-infrared wavelengths are wavelength-converted to visible wavelengths through multiple cascaded wavelength conversion operations. Existing high efficiency single-photon detectors are employed to detect an original optical signal. An embodiment of a three-stage optical wavelength converter shifts the wavelength of weak mid-infrared signals to visible wavelengths to take advantage of better photon detectors for wavelengths in the visible range. The sensitivity of photodetection techniques is enhanced by employing several cascaded frequency upconversion processes for the frequency of a photon to be detected. Each of the several optical frequency converters is configured to sequentially convert a wavelength/frequency of photons of the optical source in a monotonic sequence to a final wavelength/frequency. A single-photon photodetector is coupled to an output of the several optical frequency converters to detect single photons produced by the optical source.

Existing silicon avalanche photodiodes can be used for photons in the visible wavelength range, which is about 380 to 750 nm for humans. This is due in large part to the high efficiency and low noise of silicon avalanche photodiodes and lack of high performance single-photon detectors for the mid-infrared wavelength range. While transition edge sensors are, in principle, sensitive to mid-infrared wavelengths, the sensors currently require sophisticated cryogenic cooling and have very limited counting rates due to their slow response. High single-photon detection efficiency of mid-infrared signals is achieved using novel Chi(3) nonlinear materials and optical four-wave mixing, and optionally using standard Chi(2) nonlinearity of periodically polled lithium niobate ("PPLN") for the final wavelength-conversion stage. A ten decibel improvement in signal-noise-ratio ("SNR") performance can thereby be obtained, even in the presence of imperfect frequency-conversion efficiency. This enables sensitive single-photon detection of four micrometer ("μm") wavelength signals for enhanced remote sensing.

An advantage of using multiple steps of upconversion is that each step can be tailored to a specific configuration to improve efficiency and to reduce the noise contribution to the remaining steps. Using multiple steps enables one to select the proper nonlinear materials for efficient conversion and transmission at long wavelengths in the first step and for successively shorter wavelengths in following steps.

Employing multiple steps also enables the use of filtering between upconversion steps to reduce broadband optical background noise that arises from using strong pumps in the nonlinear conversion steps. This reduces noise from any given step from being upconverted in a previous step, thus reducing system noise. For example, a second step can be designed such that the step has negligible probability for upconverting photons leaked from the preceding stage's laser pump due to imperfect filter isolation of the first step. The process also actively filters out potential noise photons.

To obtain improved performance, the input optical signal, pump, and upconverted signal remain in a single transverse spatial mode. The size of the nonlinear material waveguide (be it in fiber, ring resonator (resonant optical ring cavity), or other waveguide) accommodates a single mode for a relatively narrow wavelength range. Thus, even if a single-step process has sufficient conversion bandwidth and transparency, the efficiency of the process will suffer for wide wavelength shifts as single spatial mode characteristics will not be preserved for sufficiently wide bandwidths. By using several steps, the process keeps the input optical signals and output upconverted photons in a single spatial mode while each step reduces the mode field diameter such that the process benefits from a single mode for a shorter wavelength conversion process. By converting over such wide bandwidths via multiple conversion steps, it is possible to move mid-infrared and longer wavelength photons to higher energy wavelengths, thereby realizing single-photon detection capability for wavelength regimes where single photons are not readily available or have poor performance.

The use of a nonlinear optical process to shift wavelength of single photons for detection has been previously described. (See, "NIR Single Photon Detectors with Up-Conversion Technology and its Applications in Quantum Communication Systems", by Ma, et al., Advances in Lasers and Electro Optics, Book edited by Nelson Costa and Adolfo Cartaxo, ISBN 978-953-307-088-9, pp. 838, April 2010, which is incorporated herein by reference.) A central focus of conventional practice has been to use Chi(2) materials (and particularly periodically polled materials to obtain sufficient conversion efficiency) in a single upconversion step. Sum-frequency generation was employed to convert about 1550 nm photons to wavelengths detectable by silicon detectors. One group investigated single-step Chi(2) conversion of classical signals from mid-infrared wavelengths (4.5 to 9.3 μm) to a wavelength that can be detected by a silicon detector, but with conversion efficiency too low to be useful for single-photon detection. (See, "Detection of Mid-IR Radiation Bysum Frequency Generation for Free Space Optical Communication," by Karstad, et al., Optics and Lasers in Engineering 43, pp. 537-544, 2005, which is incorporated herein by reference.)

There has been a proposal and demonstration to use a two-step cascade for conversion with periodically polled Chi(2) nonlinearities. (See, "Influence of Domain Disorder on Parametric Noise in Quasi-Phase-Matched Quantum Frequency Converters," by Pelc, et al., Optics Letters, Vol. 35, No. 16, p. 2804, 2010, and "Cascaded Frequency Upconversion for High-Speed Single-photon Detection at 1550 m," by Pelc, et al., Optics Letters Vol. 37, No. 4, p 476, 2012, which are incorporated herein by reference). This approach does not greatly improve conversion bandwidth as the two steps are integrated into a single crystal and share a single laser pump. Periodically polled Chi(2) materials require temperature stabilization to maintain conversion efficiency and as such are unsuitable for many field systems. As introduced herein, the process utilizes Chi(3) based materials are utilized by Nowak, et al. Extending applicability to the single-photon regime (See, "Low-power high-efficiency wavelength conversion based on modulational instability in high-nonlinearity fiber," by Nowak, et al., Optics Letters, Vol. 23, No. 12, p. 936, 1998, which is incorporated herein by reference.)

Unlike for periodically polled Chi(2) processes, the process herein does not require precise temperature stabilization for high conversion efficiency. Further, a multi-step approach as introduced herein greatly extends possible conversion bandwidth by using selected laser pump wavelengths and materials for each step such that direct detection with silicon detectors is possible after wavelength conversion from mid-infrared wavelengths. Upconversion detectors are an active area of research, but typically seek to convert photons over only a relatively limited bandwidth due to several material constraints including limited conversion bandwidth, limited transparency window and limited wavelength support for single-mode operation.

Wavelength conversion of signals from one commonly used telecom wavelength to another in dispersion shifted fiber is possible. The technique uses a Chi(3) based nonlinear effect known as modulation stability in which deviations of the optical waveform are reinforced by nonlinearity of the transmission material, resulting in sideband generation. It can be predicted that a γPL product for the optical medium of about 0.88 should be targeted to reach unit conversion efficiency, where γ is the optical material nonlinear coefficient, P is the peak pump power, and L is the length of the nonlinear optical material. Higher values of γPL result in an amplification gain, which can make up for imperfect efficiency in the final detector. With constant γPL of about 0.88, to reach near-unity conversion efficiency, the nonlinear coefficient of the optic material and its length employed for multiple steps can be estimated, each with a sufficient bandwidth. Due to the low nonlinearity of dispersion shifted fiber, it would use a prohibitive number of distinct conversion steps to wavelength-convert 1550 nm light to 800 nm light, where an single-photon detector can be efficiently applied. The conversion bandwidth is proportional to $(\gamma P)^{1/2}$. It is assumed that an upper limit for pump power is about one watt ("W"). The impact of available nonlinear materials on conversion bandwidth is herein considered.

The frequency upconversion process employed in an embodiment employs four-wave mixing ("FWM") in a Chi (3) nonlinear optical material with a pump wavelength near the zero dispersion wavelength of the optical fiber to convert signal wavelengths from four μm to 1.55 μm in two steps. It employs chalcogenide photonic crystal ("CG PC") fiber and indium gallium arsenide ("InGaAs") PIN photodiodes or avalanche photodetectors ("APDs"). A third step to convert the signal wavelengths from 1.55 μm to 0.8 μm is then performed with the chalcogenide photonic crystal, or alternatively, without limitation, with periodically polled lithium niobate. Each of the several optical frequency converters can utilize Chi(3) nonlinear optical interactions for the several waveform conversion steps. The optical frequency converters can also utilize any combination of Chi(2) and Chi(3) nonlinear optical interactions for the several waveform conversion steps.

The signal-to-noise ratio ("SNR") impact of using a three-step wavelength conversion process to shift a weak signal from four μm to 0.8 μm is estimated. A design employing a plurality of wavelength conversion processes can result in about ten decibel improvement in SNR, even with imperfect frequency upconversion. The analysis reveals that as wavelengths get shorter, a higher product of pump power and nonlinear coefficient of the material is necessary to convert an input optical signal over the same bandwidth.

Figure 5:
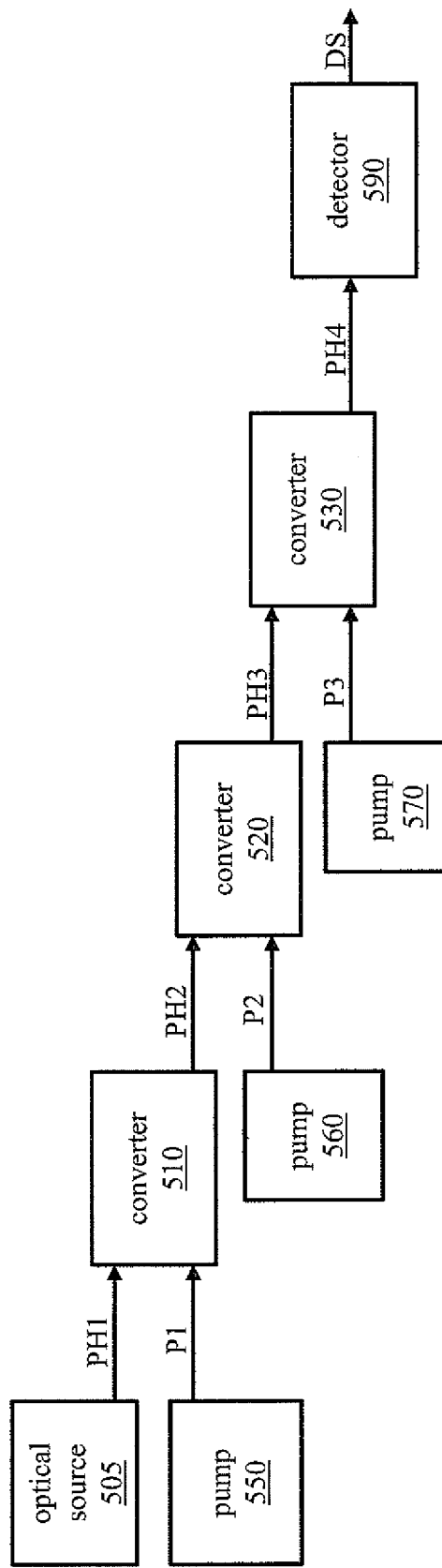
FIG. 5 illustrates a block diagram an embodiment of a photodetection system.

Turning now to FIG. 5, illustrated is a block diagram an embodiment of a photodetection system. The photodetection system demonstrates a sequence of cascaded wavelength conversion steps to convert a single mid-infrared four μm photon (a first photon designated "PH1") from an optical source 505 to a single 0.8 μm photon (a fourth photon designated "PH4", also a final photon with a final wavelength), which is at the edge of visible wavelengths. The fourth photon PH4 is then detected in silicon single-photon detector 590 to produce a detection signal DS. The sequence of cascaded wavelength conversion steps enables the use of existing silicon avalanche photodiode ("APD") single-photon detectors that have low noise and high efficiency. A three-stage frequency conversion of a four μm photon (the first photon PH1) is feasible to provide high conversion and detection efficiency with current Chi(3) materials and technology.

An assumption for multi-stage wavelength conversion includes that a zero dispersion wavelength is 0.6 nanometers ("nm") shorter than the pump wavelength with third order dispersion of 0.03 ps/(nm km), wherein "km" is kilometer. Other assumptions are that continuous wave ("CW") laser pumps are employed with maximum power greater than or equal to one watt, and the optical materials support low-loss single-mode wave guiding of the wavelengths in each step. The use of pulsed pumps relaxes the average power requirements, but would employ additional overhead for synchronization and walk off to achieve a useful time overlap of the pump and single photon.

The design methodology can be described with three steps. In a first step, the frequency of the incoming first photon PH1 is upconverted in frequency with a first optical frequency converter 510 operable in conjunction with a first pump input P1 from a first pump 550 (e.g., a laser having a wavelength of 3.5 μm) to produce a second photon PH2 having a wavelength of three μm. In the first step, requirements on γ (about 580/W km) and L (about 1.6 meters) indicate that several optical materials are available to achieve unit detection efficiency without photon loss. In a second step, the frequency of the second photon PH2 is upconverted in frequency with a second optical frequency converter 520 operable in conjunction with a second pump input P2 from a second pump 560 (e.g., a laser having a wavelength of 2.275 μm) to produce a third photon PH3 having a wavelength of 1.55 μm. In a third step, the frequency of the third photon PH3 is upconverted in frequency with a third optical frequency converter 530 operable in conjunction with a third pump input P3 from a third pump 570 (e.g., a laser having a wavelength of 1.064 μm) to produce a fourth photon PH4 having a final wavelength of 0.8 μm.

Thus, the first, second and third cascaded optical frequency converters 510, 520, 530 produce second, third and fourth photons PH2, PH3, PH4 with wavelengths lying in a monotonic sequence from a wavelength of the first photon PH1 (e.g., having a mean photon number less than one) produced by the optical source 505 to a wavelength of the third optical frequency converter 530. The first, second and third cascaded optical frequency converters 510, 520, 530 may employ an optical four-wave mixing process to produce the respective second, third and fourth photons PH2, PH3, PH4 using Chi(3) or, a combination of Chi(3) and Chi(2), nonlinear optical interactions.

Figure 6:
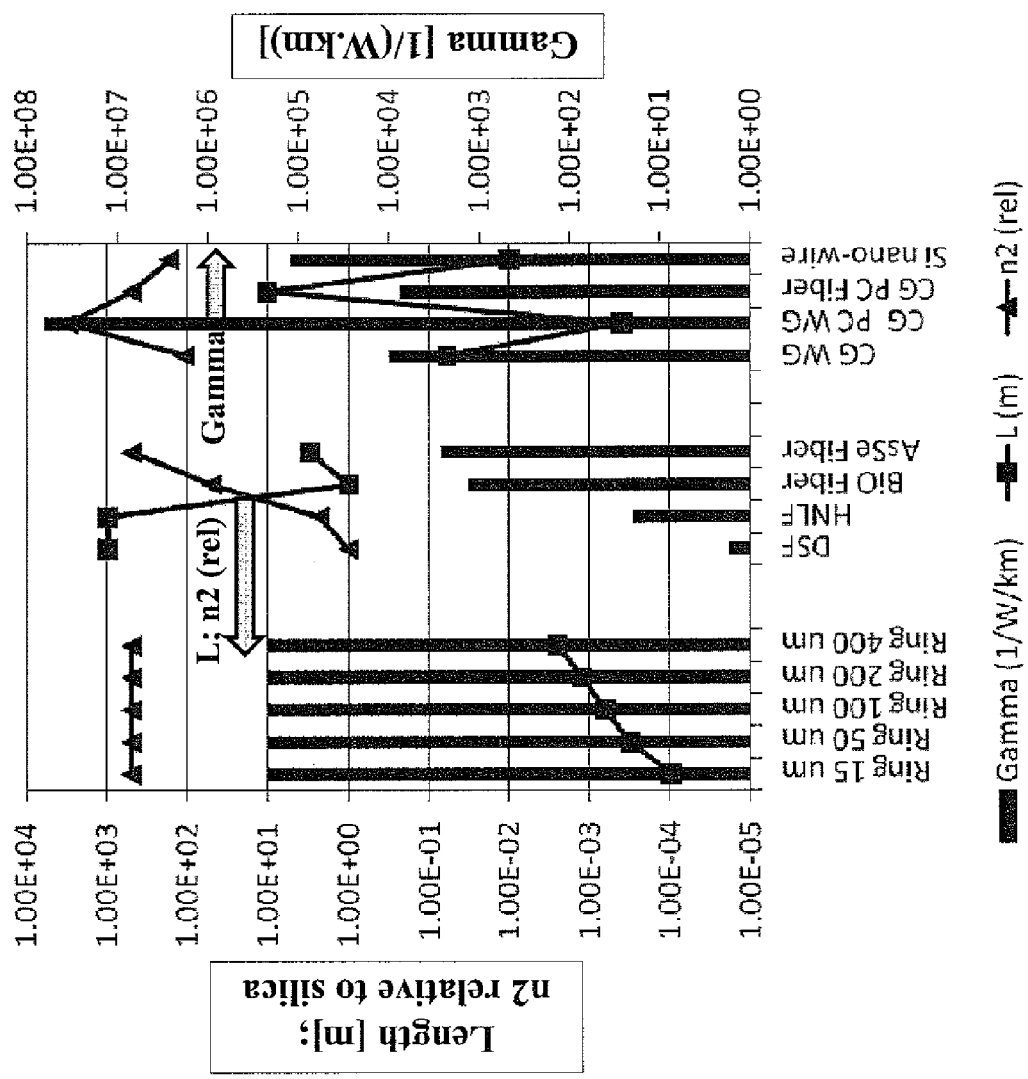
FIG. 6 illustrates a graphical representation of achieved lengths of nonlinear optical materials and the nonlinear coefficient γ for the photodetection system of FIG. 5.

Turning now to FIG. 6, illustrated is a graphical representation of achieved lengths (squares) of nonlinear optical materials (left-side vertical axis) and the nonlinear coefficient γ (bars plotted on right-side vertical axis) for the photodetection system of FIG. 5. The calculated materials requirements are shown corresponding to thresholds plotted on the plot. This plot helps in determining which materials meet the minimum required length and nonlinearity for a given conversion step. In the first step (from four μm to three μm), requirements on γ (about 580/W km) and L (about 1.6 m) indicate that the useful fibers for the first step include chalcogenide photonic crystal ("CG PC") fiber, bismuth oxide ("BiO") fiber and arsenic selenide ("AsSE") fiber.

In the second step, the frequency of the previously upconverted photon is further upconverted, and its wavelength is now reduced from three μm to 1.55 μm. For shorter wavelengths, the optical material demands continue to increase such that chalcogenide photonic crystal fiber is a presently practical material with the required length and nonlinearity. In the second step, requirements on γ (about 2900/W km) and L (about 0.31 m) indicate that the optical fiber material chalcogenide photonic crystal is available to achieve useful conversion bandwidth and conversion efficiency.

In the third step, the frequency of the previously upconverted photon is further upconverted, and its wavelength is now reduced from 1.55 μm to 0.8 μm. As in the second step, the optical material demands increase and the chalcogenide photonic crystal fiber is an existing Chi(3) material with the required length and nonlinearity for this upconversion step. Other embodiments could instead replace this step with a Chi(2) based conversion such as those based on periodically polled lithium niobate. In the third step, requirements on γ (about 5900/W km) and L (about 0.15 m) indicate that the optical fiber material chalcogenide photonic crystal provides the necessary conversion bandwidth and conversion efficiency to achieve unity detection efficiency.

To quantify the benefits of using a Chi(3) based upconversion single-photon detector, it can be compared to existing photodetectors. The ratio of signal-to-noise ratios ("SNRs") for single-photon detection of an upconversion element in combination with a short wavelength detector relative to a long wavelength detector without an optical nonlinear element was calculated. For a fair comparison, non-unit upconversion efficiency ("$\eta_{UC}$") and additional noise probability ("$P_{UC}$") due to the upconversion process were included in the assessment. The calculation also includes efficiency and dark count probability of each candidate detector.

This result is calculated by assuming the SNR of a single photon entering a given detector can be calculated by dividing the detection efficiency by the noise count probability of the detector. For the existing detector, this is the ratio of the detection efficiency divided by the dark count probability. In the case of an upconverting detector, detection efficiency is the product of upconversion efficiency and the detection efficiency of the silicon avalanche photo diode while the noise probability is the sum of the dark count probability of the silicon avalanche photo diode and the probability of measuring an excess noise photon from the upconversion process. The SNR of the upconversion detector is then divided by the SNR of the existing detector.

A single-photon counting detector with one photon incident has an SNR=η/P, where η is detection efficiency and P is the dark count probability per gate time.

The SNR advantage for upconversion detection is $$10 \text{Log}_{10}\left[\frac{\eta_f \eta_{uc} P_i}{\eta_i (P_f + P_{uc})}\right],$$

Where subscript "i" in this case denotes the performance of the initial long-wavelength detector, subscript "f" denotes the performance of the final short-wavelength detector, and the subscript "uc" denotes imperfect efficiency and excess noise from upconversion.

To make a fair comparison, the SNR improvement of the final step is quantified, which is the most difficult step of the conversion process due to the more stringent materials requirements. An InGaAs/Indium Phosphide ("InP") avalanche photodiode optimized for light detection and ranging applications was compared with upconversion followed by a silicon avalanche photo diode detector.

Figure 7:
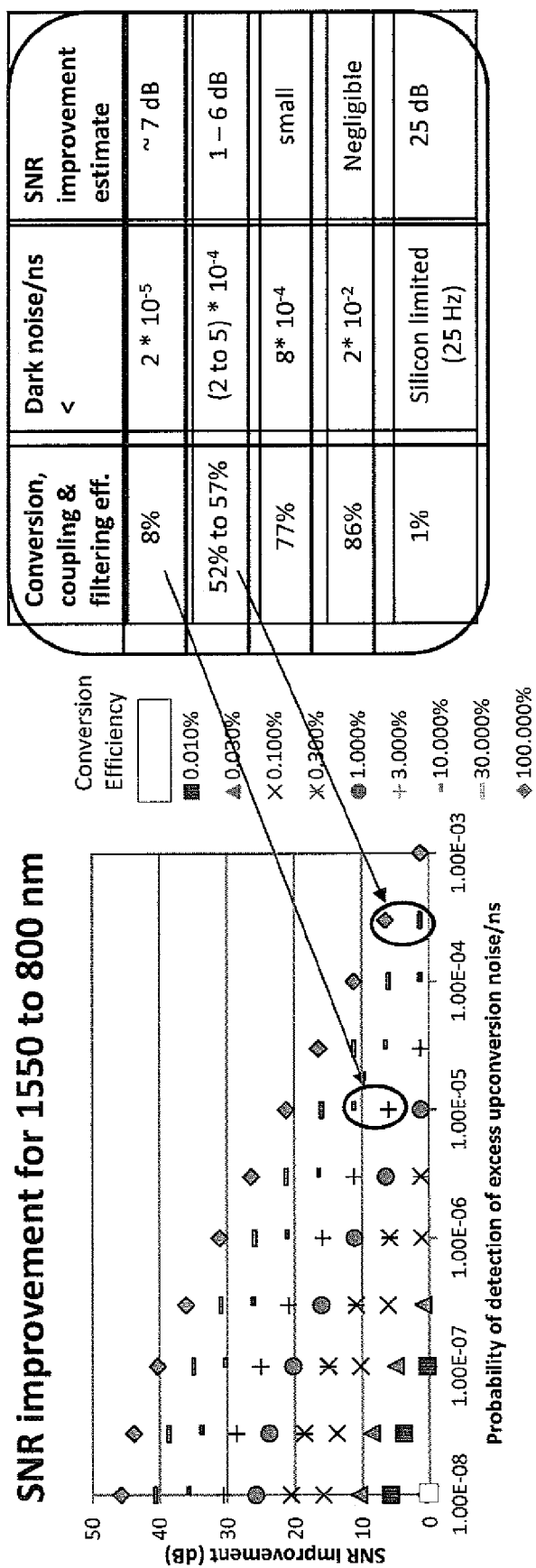
FIG. 7 illustrates a graphical representation of exemplary signal-to-noise ratio improvements for various wavelength conversion efficiencies with a photodetection system as described herein and an accompanying table illustrating exemplary dark noise and signal-to-noise improvement estimates for several conversion, coupling and filtering efficiencies.

Turning now to FIG. 7, illustrated is a graphical representation of exemplary signal-to-noise ratio improvements (left-side vertical axis) for various wavelength conversion efficiencies as shown on the right of the chart for wavelengths between 1550 nm and 880 nm with a photodetection system as described herein (see, e.g., the photodetection system of FIG. 5). FIG. 7 also illustrates a table illustrating exemplary signal-to-noise improvement estimates for several dark noise values and efficiencies that include imperfections in conversion, coupling and filtering efficiencies. To estimate the noise and imperfect conversion efficiency that can be expected from the upconversion process, recent literature of Chi(2) based periodically polled lithium niobate upconversion experiments was surveyed. Not counting losses, 99 percent conversion efficiency has been reported for periodically polled lithium niobate based upconversion from about 1.55 μm to visible wavelengths. (See, A. P. VanDevender and P. G. Kwiat, J. Of Mod. Opt.; 51, pp. 1433-45, 2004, which is incorporated herein by reference.) Values for various implementations for upconversion efficiency and dark noise are shown in the rows in the table on the right side of FIG. 7, along with a single hypothetical value of one percent conversion, coupling and filtering efficiency in the last row. Using these values, as illustrated in the graphical representation of FIG. 7, up to about seven decibel improvement in SNR can be predicted and up to a 25 decibel improvement in SNR when the upconversion process produces no excess noise, even if its efficiency is only one percent.

Table I below compares dark count probability and efficiency of two available InGaAs/InP and silicon avalanche photo diodes at 1.55 μm and at 0.8 μm, respectively.

TABLE I

| Detector | Technology | Efficiency | Dark Count Probability/ns | Active Size |
|---|---|---|---|---|
| Initial 1.55 μm | InGaAs/InP APD | 5% | $1.12*10^{-4}$ | 156 μm × 156 μm 16-element array |
| Final 0.8 μm | Si APD | 60% | $2.5*10^{-8}$ | 175 μm diameter |

A design methodology has been presented and SNR enhancements have been quantified when mid-infrared wavelength is converted to the visible range so that high performance silicon avalanche photo diodes can be employed. It has been shown that two to three conversion steps makes targets for the material nonlinear coefficient and pump power more reasonable. Conversion from four μm to 1.55 μm in two steps is possible using chalcogenide photonic crystal fiber, and then detecting the resulting short-wavelength photons with InGaAs PIN or avalanche photo diodes. A third step from 1.55 μm to 0.8 μm places the highest requirements on the nonlinear material but can be done with chalcogenide photonic crystal fiber or with a Chi(2) nonlinearity such as periodically polled lithium niobate. Further, about ten decibel improvement in SNR is can be achieved even with imperfect upconversion.

Thus, a photodetection system and method of operating the same have been introduced herein. In one embodiment, the photodetection system includes a cascaded plurality of optical frequency converters coupled to an optical source, each of the plurality of optical frequency converters being configured to sequentially convert a wavelength of photons of the optical source to a final wavelength. The photodetection system also includes a single-photon photodetector coupled to the plurality of optical frequency converters to detect single photons produced by the optical source. The plurality of cascaded optical frequency converters are configured to produce photons with wavelengths lying in a monotonic sequence from a wavelength of photons produced by the optical source to a wavelength of a final one of the plurality of optical frequency converters. The plurality of optical frequency converters are configured to utilize an optical four-wave mixing process. The plurality optical frequency converters are also configured to utilize Chi(3), or a combination of Chi(2) and Chi(3), nonlinear optical interactions. An optical input signal produced by the optical source may have a mean photon number less than one.

The photodetection system may also include a plurality of pumps configured to provide pump inputs to respective ones of the plurality of optical frequency converters. Each of the plurality of pumps may include a laser having a selected wavelength and/or a continuous wave laser pump with a maximum power greater than or equal to one watt. The single-photon photodetector may be a silicon avalanche photodiode single-photon detector.

A further process is introduced to construct an enhanced sensitivity transducer for bio-sensing and other sensitive molecular detection applications that employs dispersion engineered nonlinear resonant optical structures. An embodiment of a photonic sensor employs a four-wave mixing process in an integrated ring resonant structure. The photonic sensor can be used for sensitive biosensing applications with the detection of a small quantity of a hazardous substance.

In quantum information processing and remote sensing applications, a received signal intensity is highly attenuated, and improving the sensitivity of the detectors is important for enhanced system performance. For such signals, optical phase-sensitive amplifiers can provide improved performance because such amplifiers introduce lower quantum noise compared to phase-insensitive amplifiers. Both phase-insensitive optical parametric amplifiers and optical phase-sensitive amplifiers are employed for low-level signals such as single photons so that the composite single-photon detection system including of a pre-amplifier along with the photodetector can have enhanced detection efficiency.

A particular biosensing application is concerned with identifying an unknown molecular species in solution. A process for accomplishing this task is to attach a selective molecular sensor to a transducer element that can be read out with an optical signal. Selectivity is obtained by the molecular sensor, to which the specific species to be detected will bind. When bound to the sensor, a change in the physical properties of the sensor occurs. This change is then transduced into an effect that can be interrogated by an optical signal, detected and remotely analyzed. A technique for doing this entails attaching a molecular sensor to an integrated optical resonant cavity such as a resonant optical ring cavity.

When the target molecule binds to the molecular sensor, a change in the local refractive index surrounding the ring cavity takes place. This results in a shift of a resonance peak of the ring cavity, and the shift can be read out employing a spectroscopic technique in which a tunable laser is used to scan the resonant peak. However, there is a sensitivity limit to this process. (See, "Label-Free Biosensor Arrays Based on Silicon Ring Resonators and High-Speed Optical Scanning Instrumentation," by Iqbal, et al., J. Sel Topics in Quantum Electronics 16, pp. 654-661, 2010, which is incorporated herein by reference.) Combining the selective behavior of a ring resonator mode with a nonlinear photonic response significantly increases selectivity of the detection process.

The detector detects changes in an idler power. The resonant optical ring cavity is constructed of a highly nonlinear photonic material so that an idler is generated through a process of four-wave mixing. A target molecule is detected when idler power reduces significantly due to a combination of a shift in a resonance peak due to a refractive index change and reduction in conversion efficiency of the four-wave mixing. The result is that the sensitivity to detection of the target molecule is enhanced significantly through the use of optical four-wave mixing.

As introduced herein, a nonlinear optical material is employed for construction of the ring cavity to increase the sensitivity of the ring cavity readout. Linear spectroscopy is not used to scan the shift of the resonance peak, but instead the efficiency of a four-wave mixing process taking place in the cavity is monitored. Fortuitously, the same conventional materials can be used in this improved process, since silicon has a significant nonlinear optical activity. In a resonant optical ring cavity made from a nonlinear optical material, the process of four-wave mixing occurs when it is pumped with a high peak power. Frequencies of the high power pump and a probe (called a signal) are chosen to overlap with resonant frequencies of the resonant optical ring cavity.

Prior approaches utilize a change in a local refractive index surrounding a ring cavity due to binding of a target molecule to the sensor. This results in a shift of the resonance peak of the ring cavity, and this shift is read out with a spectroscopic technique in which a tunable laser is used to scan the resonant peak. In the process of four-wave mixing introduced herein, the sensitivity of detection of a target molecule is enhanced.

The process of non-degenerate four-wave mixing generates an idler at an equally spaced frequency from the pump as the signal, which also overlaps with a resonant frequency of the resonant optical ring cavity. The four-wave mixing conversion efficiency is given by Van, et al.:

$$\eta = \left|\frac{n_2 \omega_c}{A_{eff} c} P_i^{(p)} L'\right| (FE_p)^4 (FE_s)^2 (FE_c)^2$$

where FE is the field enhancement inside the resonator at resonance with the subscripts "p", "s", and "c" denoting field enhancement for the pump "p", signal "s", and idler "i" (or conjugate signal c). (See, "Optical Signal Processing Using Nonlinear Semiconductor Microring Resonators," by Van, et al. J. Sel Topics in Quantum Electronics 8, pp. 705-713, 2002, which is incorporated herein by reference.)

On resonance and at critical coupling, this FE can be expressed as;

$$(FE)^2 = F/\pi = \frac{\pi^2}{|\kappa|^2},$$

where L' is an effective length given by:

$$L' = L \exp(-\alpha L/2) \left|\frac{1 - \exp(-\alpha L + j\Delta kL)}{\alpha L - j\Delta kL}\right|.$$

Here, L is the circumference of the ring, $n_2$ is the nonlinear optical index, $\omega_c$ is the angular frequency of the optical signal, $A_{eff}$ is the effective mode area of the waveguide, $Pi^{(p)}$ is the pump peak pump power, F is the ring finesse, $\kappa$ is the ring coupling ratio, $\alpha$ is the propagation loss in the ring, and $\Delta k$ is the phase mismatch which, for simplicity, can be assumed to be zero in the calculations.

When a change in the local refractive index surrounding the ring cavity takes place, it results in a shift of the resonant peak of the ring cavity. The idler power is reduced since it no longer overlaps the ring resonant frequency. Also, the nonlinear interaction is diminished due to reduced pump power. To calculate the change in idler power in the ring, the field inside the ring $E_r(\phi)$ can be expressed as a function of phase shift due to the wavelength shift:

$$|E_r(\phi)|^2 = \frac{\kappa^2}{1 + \tau^4 - 2\tau^2 \cos(\phi)} |E_1|^2,$$

where $$\phi = 2\pi \left(n_0 + n_2 \frac{P_r}{A_{eff}}\right) k_0 R$$

$$\sim 2\pi n_{eff} R \frac{2\pi}{\lambda_0 + \Delta\lambda},$$

and where $E_1$ is the field produced by the pump at the input end of the optical waveguide, $\tau$ is a transmission coefficient, and the parameter $\phi$ represents the total round-trip phase shift in the resonant ring. Wavelength shifts on the order of one picometer ("pm") or less are considered, which is a resolution limit of the linear transmission shift method.

Figure 8:
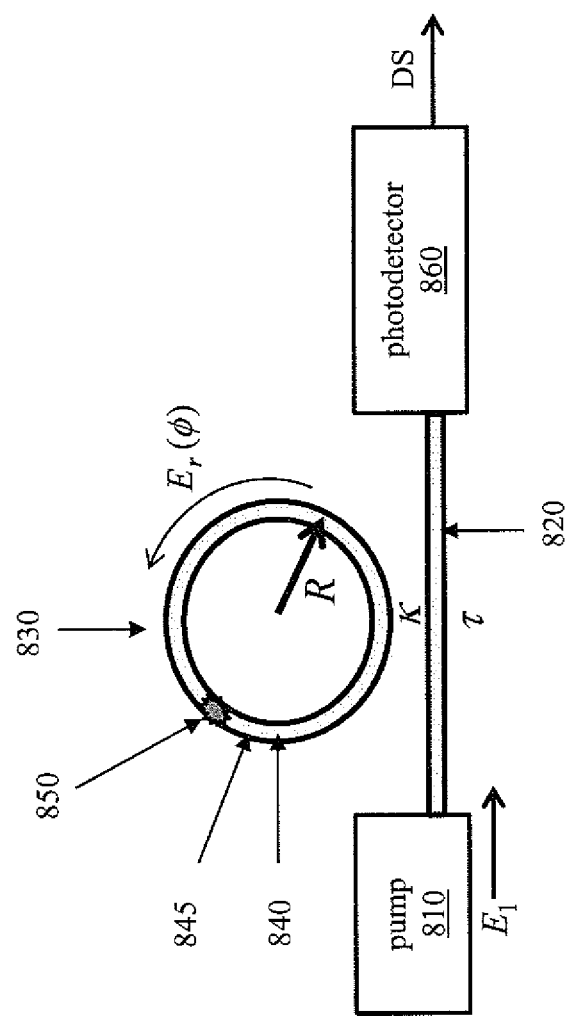
FIG. 8 illustrates a system level diagram of an embodiment of an optical sensor.

Turning now to FIG. 8, illustrated is a system level diagram of an embodiment of an optical sensor. The optical sensor includes a transducer including a nonlinear resonant optical ring cavity 830 having a radius R of about 15 μm and containing a highly nonlinear optical material 840 such as silicon or chalcogenide glass in a cavity thereof. A selective coating 845 to detect the biological target is applied to an exposed surface of the highly nonlinear optical material 840 that is formed in the optical ring cavity 830. A high power pump 810 with field $E_1$ at an input end of an optical waveguide 820. The process of non-degenerate four-wave mixing in the resonant optical ring cavity 830 generates a signal and an idler at equally spaced frequencies from the pump 810. All three waves overlap with resonant frequencies of the optical ring cavity 830. The pump 810 thus induces an idler field $E_r(\phi)$ in the optical ring cavity 830. The transmission coefficient parameter $\tau$ is related to the ring coupling coefficient $\kappa$ by $|\tau|^2 + |\kappa|^2 = 1$.

A photodetector 860 is coupled to an output end of the optical waveguide 820, and measures a power of the idler. The coating 845 is configured to change a refractive index of the optical ring cavity 830 in response to an external stimulus 850 (e.g., a biological target such as a biological tissue), to which the coating 845 is selectively sensitive. When a change in the local refractive index surrounding the optical ring cavity 830 takes place, it results in a shift of the resonant peak of the optical ring cavity 830. The idler power is reduced since it no longer overlaps with the resonant frequency of the optical ring cavity 830. The nonlinear four-wave mixing interaction is highly diminished due to reduced pump power. When the external stimulus 850 settles on the coating 845, the photodetector 860 measures a change in the power of the idler at the output end of the optical waveguide 820, thereby producing a detected signal DS indicating detection of the external stimulus 850.

The nonlinear process of four-wave mixing may be utilized to increase the selectivity or sensitivity of sensing systems, predominantly in the transducer operation. In nonlinear resonant ring structures, the parametric gain varies exponentially with the pump power. Monitoring the efficiency of the four-wave mixing process that takes place in the resonant optical ring cavities rather than employing linear spectroscopy to scan the shift of the resonant peak leads to increased sensing sensitivity. Further, the detection of a change in efficiency is a simpler and more cost effective solution over spectroscopic detection.

Figure 9:
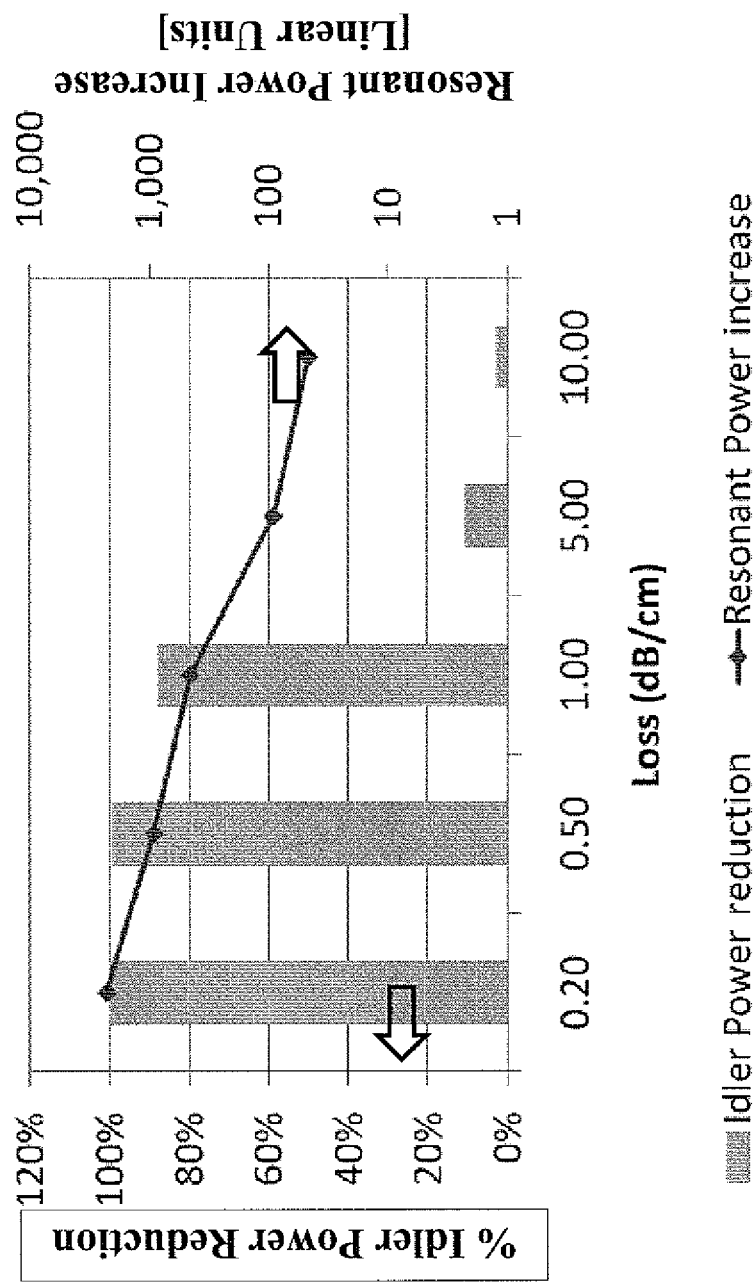
FIG. 9 illustrates a graphical representation showing reduction in idler power as a function of the propagation loss in a resonant optical ring cavity.

Turning now to FIG. 9, illustrated is a graphical representation showing reduction in idler power as a function of the propagation loss in a resonant optical ring cavity (assuming parameters for a silicon resonant optical ring cavity). It assumes that the resonant peak shift is 0.5 picometers ("pm"), which corresponds to $8 \times 10^{-7}$ refractive index units change and a 15 μm optical ring cavity. Significant reduction in idler power is observable at losses as high as ten decibels/centimeter ("dB/cm"), provided there is sufficient nonlinearity to generate observable idler power levels. No nonlinearity computation is done here, which assumes that an idler is observable above the noise floor.

Figure 10:
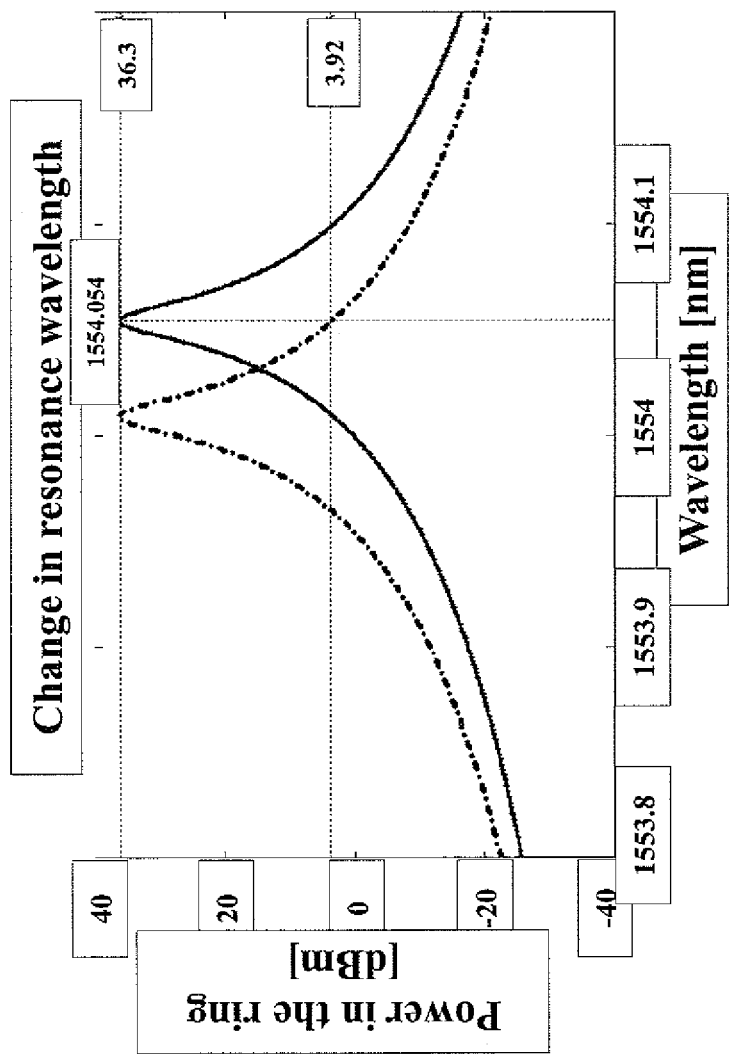
FIG. 10 illustrates a graphical representation showing an exemplary reduction of idler power obtained employing a linear shift process without four-wave mixing in a resonant optical ring cavity.
Figure 11:
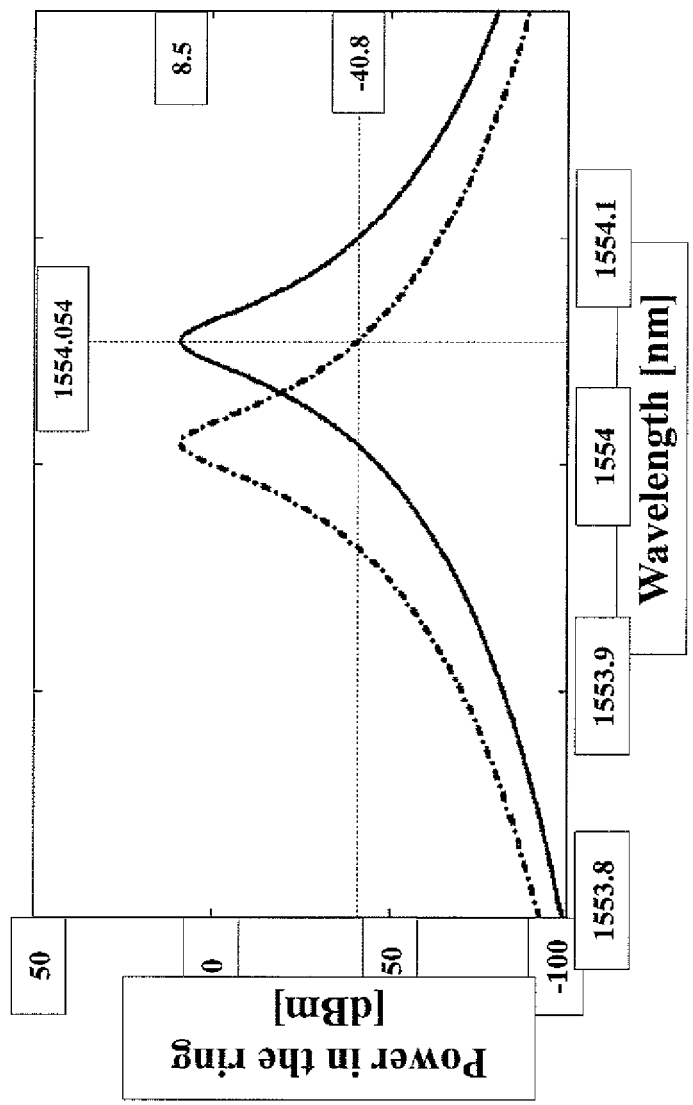
FIG. 11 illustrates an exemplary enhanced sensitivity that can be obtained by utilizing a resonant optical ring cavity combined with an optical nonlinearity.

Turning now to FIG. 10, illustrated is a graphical representation illustrating an exemplary reduction of idler power obtained employing a linear shift process without four-wave mixing in a resonant optical ring cavity. FIG. 11 illustrates an exemplary enhanced sensitivity that can be obtained by utilizing a resonant structure combined with an optical nonlinearity. In both FIGURES, the vertical axes of the graphs represent power in the optical ring cavity expressed in decibels ("dB") referenced to a milliwatt ("mW"). FIG. 10 shows about a 32.4 dB change in idler power employing a linear shift process, and FIG. 11 shows about a 49.2 dB change in idler power employing four-wave mixing in the resonant optical ring cavity. Parameters values that were used for this comparison include:

Propagation Loss: one dB/cm,
Ring coupling coefficient κ=0.2,
Index change from 3.45 to 3.4499 (0.029 percent),
Pump power=100 mW,
$n_2 = 1.3 \times 10^{-17}$ m²/W,
$A_{eff} = 0.5$ μm², and
L=400 μm.

Thus, processes have been introduced for detection of optical signals and chemical species employing nonlinear optical processes. In accordance therewith, an optical sensor and method of operating the same have been introduced herein. In one embodiment, the optical sensor includes an optical pump, and a transducer including an optical ring cavity (e.g., a nonlinear optical ring cavity and/or a resonant optical ring cavity) coupled to the optical pump and configured to utilize optical four-wave mixing to detect an external stimulus. The optical ring cavity may include a coating on a surface thereof. The coating is configured to change a refractive index of the optical ring cavity in response to the external stimulus. The optical sensor is also configured to change a state thereof in response to a change in the refractive index. The external stimulus may be a biological target including biological tissue.

The optical sensor further comprises a pump at an input end of an optical waveguide proximate the optical ring cavity and a photodetector coupled to an output end of the optical waveguide. The pump is configured to induce an idler field in the optical ring cavity. The four-wave mixing in the optical ring cavity is configured to generate a signal and an idler at equally spaced frequencies from the pump. The photodetector is configured to measure a power of the idler.

As described above, the exemplary embodiment provides both a method and corresponding apparatus consisting of various modules providing functionality for performing the steps of the method. The modules may be implemented as hardware (embodied in one or more chips including an integrated circuit such as an application specific integrated circuit), or may be implemented as software or firmware for execution by a computer processor. In particular, in the case of firmware or software, the exemplary embodiment can be provided as a computer program product including a computer readable storage structure embodying computer program code (i.e., software or firmware) thereon for execution by the computer processor.

Although the embodiments and its advantages have been described in detail, it should be understood that various changes, substitutions, and alterations can be made herein without departing from the spirit and scope thereof as defined by the appended claims. For example, many of the features and functions discussed above can be implemented in software, hardware, or firmware, or a combination thereof. Also, many of the features, functions, and steps of operating the same may be reordered, omitted, added, etc., and still fall within the broad scope of the various embodiments.

Moreover, the scope of the various embodiments is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized as well. Accordingly, the appended claims are intended to include within their scope such processes, machines, manufacture, compositions of matter, means, methods, or steps.

What is claimed is:

1. An optical sensor, comprising:
an optical pump; and
a transducer comprising an optical ring cavity coupled to said optical pump and configured to utilize optical four-wave mixing to detect an external stimulus.

2. The optical sensor as recited in claim 1 further comprising a pump at an input end of an optical waveguide proximate said optical ring cavity and a photodetector coupled to an output end of said optical waveguide, said pump being configured to induce an idler field in said optical ring cavity.

3. The optical sensor as recited in claim 2 wherein said four-wave mixing in said optical ring cavity is configured to generate a signal and an idler at equally spaced frequencies from said pump.

4. The optical sensor as recited in claim 3 wherein said photodetector is configured to measure a power of said idler.

5. The optical sensor as recited in claim 1 wherein said optical ring cavity is a nonlinear optical ring cavity.

6. The optical sensor as recited in claim 1 wherein said optical ring cavity is a resonant optical ring cavity.

7. The optical sensor as recited in claim 1 wherein said optical ring cavity comprises a coating on a surface thereof, said coating being configured to change a refractive index of said optical ring cavity in response to said external stimulus.

8. The optical sensor as recited in claim 7 wherein said optical sensor is configured to change a state thereof in response to said change in said refractive index.

9. The optical sensor as recited in claim 1 wherein said external stimulus is a biological target.

10. The optical sensor as recited in claim 9 wherein said biological target comprises biological tissue.

11. A method of operating an optical sensor, comprising:
providing an optical pump; and
coupling a transducer comprising an optical ring cavity to said optical pump and configured to utilize optical four-wave mixing to detect an external stimulus.

12. The method as recited in claim 11 further comprising providing a pump at an input end of an optical waveguide proximate said optical ring cavity and a photodetector coupled to an output end of said optical waveguide, said pump being configured to induce an idler field in said optical ring cavity.

13. The method as recited in claim 12 wherein said four-wave mixing in said optical ring cavity is configured to generate a signal and an idler at equally spaced frequencies from said pump.

14. The method as recited in claim 13 wherein said photodetector is configured to measure a power of said idler.

15. The method as recited in claim 11 wherein said optical ring cavity is a nonlinear optical ring cavity.

16. The method as recited in claim 11 wherein said optical ring cavity is a resonant optical ring cavity.

17. The method as recited in claim 11 further comprising providing a coating on a surface of said optical ring cavity, said coating being configured to change a refractive index of said optical ring cavity in response to said external stimulus.

18. The method as recited in claim 17 further comprising changing a state of said optical sensor in response to said change in said refractive index.

19. The method as recited in claim 11 wherein said external stimulus is a biological target.

20. The method as recited in claim 19 wherein said biological target comprises biological tissue.

* * * * *